United States Patent [19]

Leemans et al.

[11] Patent Number: 5,648,477
[45] Date of Patent: Jul. 15, 1997

[54] GENETICALLY ENGINEERED PLANT CELLS AND PLANTS EXHIBITING RESISTANCE TO GLUTAMINE SYNTHETASE INHIBITORS, DNA FRAGMENTS AND RECOMBINANTS FOR USE IN THE PRODUCTION OF SAID CELLS AND PLANTS

[75] Inventors: Jan Leemans, Heusden; Johan Botterman, Zwijnaarde, both of Belgium; Charles Thompson, Grand Lancy/Genege; Rao Mouva, Geneva, both of Switzerland

[73] Assignee: Plant Genetic Systems, N.V., Gent, Belgium

[21] Appl. No.: 477,320

[22] Filed: Jun. 7, 1995

Related U.S. Application Data

[62] Division of Ser. No. 525,300, May 17, 1990, Pat. No. 5,561,236, which is a continuation of Ser. No. 131,140, Nov. 5, 1987, abandoned.

[30] Foreign Application Priority Data

| Mar. 11, 1986 | [GB] | United Kingdom | 86400521 |
| Jan. 21, 1987 | [GB] | United Kingdom | 87400141 |

[51] Int. Cl.$^6$ .............. C12N 15/11; C12N 15/00; A01H 4/00
[52] U.S. Cl. .......... 536/23.7; 536/23.1; 536/23.2; 435/172.3; 435/320.1; 800/205
[58] Field of Search .......... 435/172.3, 172.1, 435/240.5; 935/75; 536/23.1, 23.7, 23.2; 800/205

[56] References Cited

U.S. PATENT DOCUMENTS 4,769,061  9/1988  Comai .......................... 71/86

FOREIGN PATENT DOCUMENTS

| 173327 | 3/1986 | European Pat. Off. |
| 196375 | 10/1986 | European Pat. Off. |
| 2007976 | 5/1979 | United Kingdom ............ A01N 9/36 |
| 84/02920 | 8/1984 | WIPO . |
| 84/20913 | 8/1984 | WIPO . |
| 86/02097 | 4/1986 | WIPO . |

OTHER PUBLICATIONS

Thompson, et al., *Gene*, vol. 20, pp. 51–62 (1982).
Mason et al., *Phytochemistry*, vol. 21, No. 4, pp. 855–857 (1982).
Thompson et al., *Journal of Bacteriology*, vol. 151, No. 2, pp. 678–685 (1982).
Thompson et al., *Proc. Natl. Acad. Sci. USA*, vol. 80, pp. 5190–5194 (1983).
Thompson et al., *Mol. Gen. Genet.*, vol. 195, pp. 39–43 (1984).
Bayer et al., *Helvetica Chimica Acta*, vol. 55, No. 25, pp. 224–239 (1972).
Fayerman et al., *Biotechnology*, vol. 4, No. 9, pp. 786–789 (Sep. 1986).
Thompson et al., *Nature*, vol. 286, No. 5772, pp. 525–527 (1980).
Velten et al. *Nucleic Acids Research*, vol. 13, No. 19, pp. 6981–6998 (1985).
Erickson et al., *Chemical Abstracts*, vol. 104, No. 9, p. 311, 64619g (Mar. 3, 1986).
Kobayashi et al., *The Journal of Antibiotics*, vol. 49, No. 5, pp. 688–693 (May 1986).

(List continued on next page.)

*Primary Examiner*—Gary Benzion
*Attorney, Agent, or Firm*—Burns, Doane, Swecker & Mathis, LLP

[57] ABSTRACT

The invention relates to a DNA fragment containing a determined gene, the expression of which inhibits the antibiotic and herbicidal effects of Bialaphos and related products.

It also relates to recombinant vectors, containing such DNA fragment, which enable this protective gene to be introduced and expressed into cells and plant cells.

30 Claims, 13 Drawing Sheets

OTHER PUBLICATIONS

Langelueddeke et al. *Chemical Abstracts*, vol. 98, p. 242, 48585v (1982).

Jones et al., *Chemical Abstracts*, vol. 104, No. 5, p. 152, 29747a (Feb. 1986).

Zalacain et al. *Nucleic Acids Research*, vol. 14, No. 4, pp. 1565–1581 (Feb. 1986).

Murakami et al., *Chemical Abstracts*, vol. 106, p. 1149, 1151u (1987).

Schreier et al. *EMBO J.*, vol. 4, pp. 25–32, (1985).

Cashmore, *Proc. Natl. Acad. Sci. USA*, vol. 81, pp. 2960–2964 (1984).

Shields, *Nature*, vol. 317, pp. 668, (1985).

Vara et al., *Gene*, vol. 33, pp. 197–206 (1985).

Worthing (Ed.), *Pesticide Manual*, 7th Ed., p. 302 (no date).

Thompson (3–8 Sep. 1984) *Genetic Engineering and Antibiotic Production*, Rev. Biol. 77(4) pp. 567–568, 1984.

Winnacker, *From Genes to Clones*, 1987, pp. 413–415.

DeCleene, *Phytopath Z.*, vol. 113, pp. 81–89, (1985).

Stalker, et al., *Science*, pp. 419–423, Oct. 21, 1988.

DeBlock, *The EMBO Journal*. vol. 6, No. 9, pp. 2513–2518, (1987).

*Journal of Cellular Biochemistry*, Abstracts, Mar. 31, –Apr. 29, 1984, Alan R. Liss, Inc., New York.

Goodman, et al., *Science*, vol. 236, pp. 48–54 (1987).

Vasil, *Biotechnology* vol. 6, pp. 397–402, (Apr. 1988).

Donn, et al., *Journal of Molecular and Applied Genetics*, vol. 2, pp. 621–635 (1985).

*Development of an Angiosperm Plant*, Chapter 16, pp. 540–546.

Murakami et al. "The bialaphos biosynthetic gene of *Streptomyces hygroscopicus:* Molecular cloning and characterization of the gene cluster". Mol. Gen. Genet. 205:42–50.

```
        CCC GCT CAA GCT CGC TGT CAT TTT CGA GAC GCC ATC TTT GGA AGC
        GGT GGC CGA ATC CGT ACT GCG CGG ACT CGA CGA CGC GTA AAA CGA
        TCG ACC ACG TAC ACG AGT CCG GAC ACG GGG CGA GGA GGC CCG GTT

CCG GCA CCG AGG AAG ACC GAA GGA AGA CCA CAC GTG AGC CCA GAA

CGA CGC CCG GCC GAC ATC CGC CGT GCC ACC GAG GCG GAC ATG CCG
FokI↑
        GCG GTC TGC ACC ATC GTC AAC CAC TAC ATC GAG ACA AGC ACG GTC

AAC TTC CGT ACC GAG CCG CAG GAA CCG CAG GAG TGG ACG GAC GAC

CTC GTC CGT CTG CGG GAG CGC TAT CCC TGG CTC GTC GCC GAG GTG

GAC GGC GAG GTC GCC GGC ATC GCC TAC GCG GGC CCC TGG AAG GCA

CGC AAC GCC TAC GAC TGG ACG GCC GAG TCG ACC GTG TAC GTC TCC

CCC CGC CAC CAG CGG ACG GGA CTG GGC TCC ACG CTC TAC ACC CAC

CTG CTG AAG TCC CTG GAG GCA CAG GGC TTC AAG AGC GTG GTC GCT

GTC ATC GGG CTG CCC AAC GAC CCG AGC GTG CGC ATG CAC GAG GCG

CTC GGA TAT GCC CCC CGC GGC ATG CTG CGG GCG GCC GGC TTC AAG

CAC GGG AAC TGG CAT GAC GTG GGT TTC TGG CAG CTG GAC TTC AGC

CTG CCG GTA CCG CCC CGT CCG GTC CTG CCC GTC ACC GAG ATC TGA
                                                             ↑BglII
        ACG GAG TGC GCG TGG GCA TCG CCC GAG TTG GAG CTG GTA CGG GAA
        CTC ATC GAA CTC AAC TGG CAT ACC GCG AAT GGT GAG GTG GAA CCG
        CGG CGG ATC GCG TAC GAC CGT GCC CAG G
```

FIG. 2

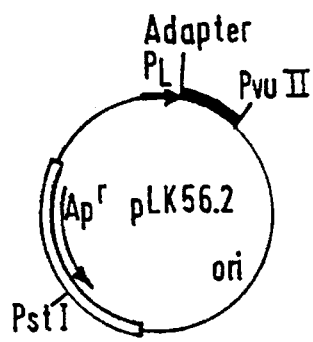
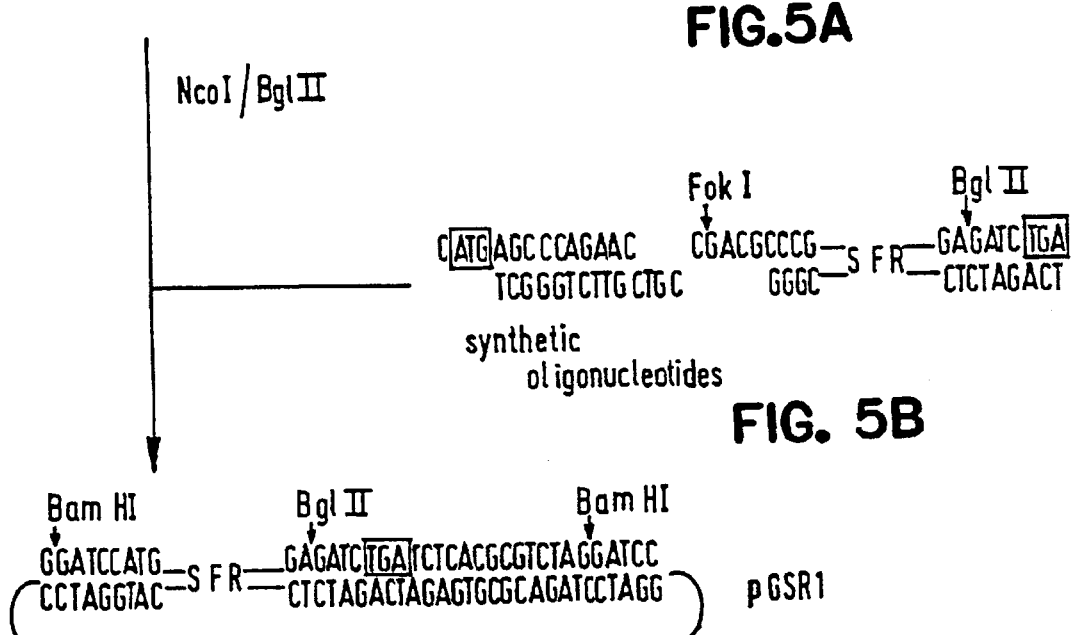
FIG. 5A
FIG. 5B
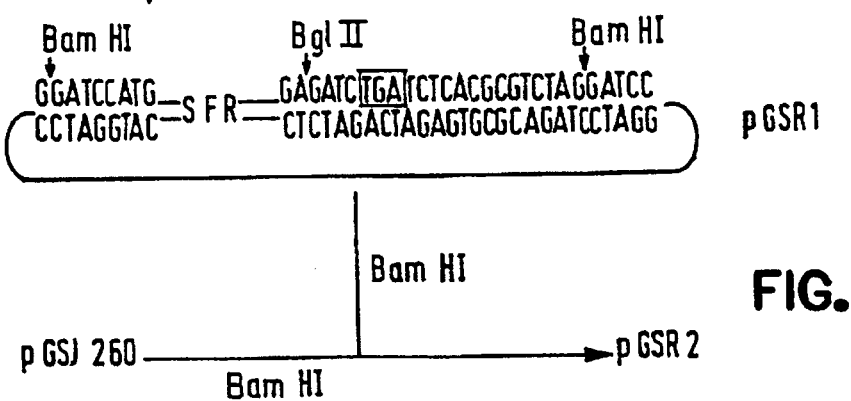
FIG. 5C

```
TAAAGAGGTGCCCGCCACCCGCTTTCGCAGAACACCGAAGGAGACCACAC
GTGAGCCCAGAACGACGCCCGGTCGAGATCCGTCCCGCCACCGCCGCCGA
CATGGCGGCGGTCTGCGACATCGTCAATCACTACATCGAGACGAGCACGG
TCAACTTCCGTACGGAGCCGCAGACTCCGCAGGAGTGGATCGACGACCTG
GAGCGCCTCCAGGACCGCTACCCCTGGCTCGTCGCCGAGGTGGAGGGCGT
CGTCGCCGGCATCGCCTACGCCGGCCCCTGGAAGGCCCGCAACGCCTACG
ACTGGACCGTCGAGTCGACGGTGTACGTCTCCCACCGGCACCAGCGGCTC
GGACTGGGCTCCACCCTCTACACCCACCTGCTGAAGTCCATGGAGGCCCA
GGGCTTCAAGAGCGTGGTCGCCGTCATCGGACTGCCCAACGACCCGAGCG
TGCGCCTGCACGAGGCGCTCGGATACACCGCGCGCGGGACGCTGCGGGCA
GCCGGCTACAAGCACGGGGGCTGGCACGACGTGGGGTTCTGGCAGCGCGA
CTTCGAGCTGCCGGCCCCGCCCCGCCCCGTCCGGCCCGTCACACAGATCT
GAGCGGAGAGCGCATGGC
```

FIG. 9

```
                  10          20           30           40          50
PBG39 ──── MSPERRRPADI RRATEADMPA  VCTIVNHVIE  TSTVNFRTEP  QEPQEWTDDL
PJS1  ────       VSPERRPVEI RPATAADMAA  VCDIVNHVIE  TSTVNFRTEP  QTPQEWIDDL 60          70           80           90          100
PBG39 ──── VRLRERYPWL VAEVDGEVAG  IAVAGPWKAR  NAYDWTAEST  VYVSPRHQRT
PJS1  ──── ERLQDRYPWL VAEVEGVVAG  IAVAGPWKAR  NAYDWTVEST  VVVSHRHQRL 110         120          130          140          150
PBG39 ──── GLGSTLYTHL LKSLEAQGFK  SVVAVIGLPN  DPSVRMHEAL  GYAPRGMLRA
PJS1  ──── GLGSTLYTHL LKSMEAQGFK  SVVAVIGLPN  DPSVRLHEAL  GYTARGTLRA 160         170          180
PBG39 ──── AGFKHGNWHD VGFWQLDFSL  PVPPRPVLPV  TEI*
PJS1  ──── AGYKHGGWHD VGFWQRDFEL  PAPPRPVRPV  TQI*
```

FIG. 10

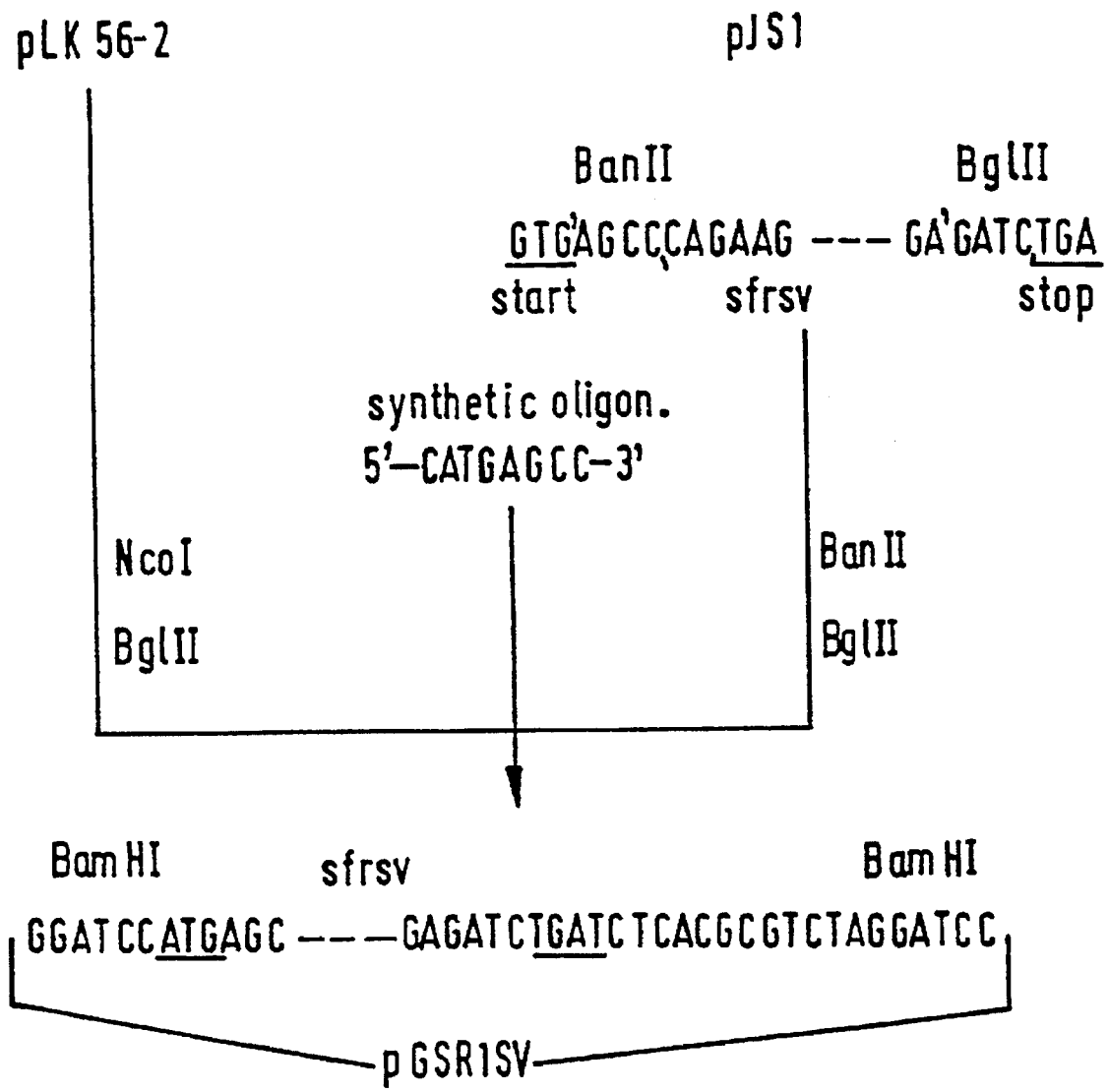
FIG. II

GENETICALLY ENGINEERED PLANT CELLS AND PLANTS EXHIBITING RESISTANCE TO GLUTAMINE SYNTHETASE INHIBITORS, DNA FRAGMENTS AND RECOMBINANTS FOR USE IN THE PRODUCTION OF SAID CELLS AND PLANTS

This application is a divisional of application Ser. No. 07/525,300, filed May 17, 1990, now U.S. Pat. No. 5,561, 236, which is a continuation of application Ser. No. 07/131, 140, filed Nov. 5, 1987, abandoned.

The invention relates to a process for protecting plant cells and plants against the action of glutamine synthetase inhibitors.

It also relates to applications of such process, particularly to the development of herbicide resistance into determined plants.

It relates further to non-biologically transformed plant cells and plants displaying resistance to glutamine synthetase inhibitors as well as to suitable DNA fragments and recombinants containing nucleotide sequences encoding resistance to glutamine synthetase inhibitors.

Glutamine synthetase (hereafter simply designated by GS) constitutes in most plants one of the essential enzymes for the development and life of plant cells. It is known that GS converts glutamate into glutamine. GS is involved in an efficient pathway (the only one known nowadays) in most plants for the detoxification of ammonia released by nitrate reduction, aminoacid degradation or photorespiration. Therefore potent inhibitors of GS are very toxic to plant cells. A particular class of herbicides has been developped, based on the toxic effect due to inhibition of GS in plants.

These herbicides comprise as an active ingredient a GS inhibitor.

There are at least two possible ways which might lead to plants resistant to the inhibitors of the action of glutamine synthetase; (1) by changing the target. It can be envisaged that mutations in the GS enzyme can lead to insensitivity towards the herbicide; (2) by inactivation of the herbicide. Breakdown or modification of the herbicide inside the plant could lead to resistance.

Bialaphos and phosphinothricin (hereafter simply designated by PPT) are two such inhibitors of the action of GS, (ref. 16, 17) and have been shown to possess excellent herbicidal properties (see more particularly ref. 2 as concerns Bialaphos).

Bialaphos has the following formula (I):

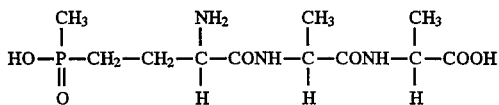

PPT has the following formula (II):

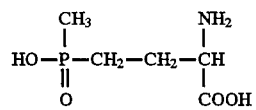

Thus the structural difference between PPT and Bialaphos resides in the absence of two alanine amino acids in the case of BPT.

These two herbicides are non selective. They inhibit growth of all the different species of plants present on the soil, accordingly cause their total destruction.

Bialaphos was first disclosed as having antibiotic properties, which enabled it to be used as a pesticide or a fungicide. Bialaphos can be produced according to the process disclosed in U.S. Pat. No. 3,832,394, assigned to MEIJI SEIKA KAISHA LTD., which patent is incorporated herein by reference. It comprises cultivating Streptomyces hygroscopicus, such as the strain available at the American Type Culture Collection, under the ATCC number 21,705, and recovering Bialaphos from its culture media. However, other strains, such as Streptomyces viridochromogenes, also produce this compound (ref. 1).

Other tripeptide antibiotics which contain a PPT moiety are or might be discovered in nature as well, e.g., phosalacin (ref. 15).

PPT is also obtained by chemical synthesis and is commercially distributed by the industrial Company HOECHST.

A number of Streptomyces species have been disclosed which produce highly active antibiotics which are known to incapacitate procaryotic cell functions or enzymes. The Streptomyces species which produce these antibiotics would themselves be destroyed if they had not a self defense mechanism against these antibiotics. This self defense mechanism has been found in several instances to comprise an enzyme capable of inhibiting the antibiotic effect, thus of avoiding autotoxicity for the Streptomyces species concerned. This modification is generally reversed when the molecule is exported from the cell.

The existence of a gene which encodes an enzyme able to modify the antibiotic so as to inhibit the antibiotic effect against the host has been demonstrated in several Streptomyces producing antibiotics, for example, in S. fradiae, S. azureus, S. vinaceus, S. erythreus, producing neomycin, thiostrepton, viomycin, and MLS (Macrolide Lincosamide Streptogramin) antibiotics respectively (ref. 4), (ref. 5), (ref. 6), (ref.14 by CHATER et al., 1982 describes standard techniques which can be used for bringing these effects to light).

In accordance with the present invention, it has been found that Streptomyces hygroscopicus ATCC 24,705, also possesses a gene encoding an enzyme responsible for the inactivation of the antibiotic properties of Bialaphos. Experiments carried out by the applicants have lead to the isolation of such a gene and its use in a process for controlling the action of GS inhibitors, based on PPT or derived products.

An object of the invention is to provide a new process for controlling the action in plant cells and plants of GS inhibitors.

Another object of the invention is to provide DNA fragments and DNA recombinants, particularly modified vectors containing said DNA fragments, which DNA fragments contain nucleotide sequences capable, when incorporated in plant cells and plants, to protect them against the action of GS inhibitors.

A further object of the invention is to provide non-biologically transformed plant cells and plants capable of neutralizing or inactivating GS inhibitors.

A further object of the invention is to provide a process for selectively protecting plant species against herbicides of a GS inhibitor type.

More specifically an object of the invention is to provide a DNA fragment transferable to plant cells- and to whole plants- capable of protecting them against the herbicidal effects of Bialaphos and of structurally analogous herbicides.

A further object of the invention is to provide plant cells resistant to the products of the class exemplified by Bialaphos, which products possess the PPT unit in their structure.

The process according to the invention for controlling the action in plant cells and plants of a GS inhibitor when contacted therewith, comprises providing said plants with a heterologous DNA fragment including a foreign nucleotide sequence, capable of being expressed in the form of a protein in said plant cells and plants, under conditions such as to cause said heterologus DNA fragment to be integrated stably through generations in the cells of said plants, and wherein said protein has an enzymatic activity capable of inactivating or neutralizing said glutamine synthetase inhibitor.

A preferred DNA fragment is one derived from an antibiotic-producing-Streptomyces strain (or a sequence comprising a nucleotide sequence encoding the same activity) and which encodes resistance to said GS inhibitors.

Preferred nucleotide sequences for use in this invention encode a protein which has acetyl tranferase activity with respect to said GS inhibitors.

A most preferred DNA fragment according to the invention comprises a nucleotide sequence coding for a polypeptide having a PPT acetyl transferase activity.

A particular DNA fragment according to the invention, for the subsequent transformation of plant cells, consists of a nucleotide sequence coding for at least part of a polypeptide having the following sequence:

cally and expressed therein, i.e., as termed hereafter "plant-protecting capability" against Bialaphos.

A preferred DNA fragment consists of the following nucleotide sequence:

```
                                                    X   SER PRO GLU
183
ARG ARG PRO ALA ASP ILE  ARG ARG ALA THR GLU ALA ASP MET PRO
228
ALA VAL CYS THR ILE  VAL ASN HIS TYR ILE  GLU THR SER THR VAL
273
ASN PHE ARG THR GLU PRO GLN GLU PRO GLN GLU TRP THR ASP ASP
318
LEU VAL ARG LEU ARG GLU ARG TYR PRO TRP LEU VAL ALA GLU VAL
363
ASP GLY GLU VAL ALA GLY ILE  ALA TYR ALA GLY PRO TRP LYS ALA
408
ARG ASN ALA TYR ASP TRP THR ALA GLU SER THR VAL TYR VAL SER
453
PRO ARG HIS GLN ARG THR GLY LEU GLY SER THR LEU TYR THR HIS
498
LEU LEU LYS SER LEU GLU ALA GLN GLY PHE LYS SER VAL VAL ALA
543
VAL ILE  GLY LEU PRO ASN ASP PRO SER VAL ARG MET HIS GLU ALA
588
LEU GLY TYR ALA PRO ARG GLY MET LEU ARG ALA ALA GLY PHE LYS
633
HIS GLY ASN TRP HIS ASP VAL GLY PHE TRP GLN LEU ASP PHE SER
678
LEU PRO VAL PRO PRO ARG PRO VAL LEU PRO VAL THR GLU ILE
723
``` in which X represents MET or VAL, which part of said polypeptide is of sufficient length to confer protection against Bialaphos to plant cells, when incorportated geneti-

```
                                                    GTG AGC CCA GAA
183

CGA CGC CCG GCC GAC ATC CGC CGT GCC ACC GAG GCG GAC ATG CCG
228

GCG GTC TGC ACC ATC GTC AAC CAC TAC ATC GAG ACA AGC ACG GTC
273

AAC TTC CGT ACC GAG CCG CAG GAA CCG CAG GAG TGG ACG GAC GAC
318

CTC GTC CGT CTG CGG GAG CGC TAT CCC TGG CTC GTC GCC GAG GTG
363

GAC GGC GAG GTC GCC GGC ATC GCC TAC GCG GGC CCC TGG AAG GCA
408

CGC AAC GCC TAC GAC TGG ACG GCC GAG TCG ACC GTG TAC GTC TCC
453

CCC CGC CAC CAG CGG ACG GGA CTG GGC TCC ACG CTC TAC ACC CAC
498

CTG CTG AAG TCC CTG GAG GCA CAG GGC TTC AAG AGC GTG GTC GCT
543

GTC ATC GGG CTG CCC AAC GAC CCG AGC GTG CGC ATG CAC GAG GCG
588

CTC GGA TAT GCC CCC CGC GGC ATG CTG CGG GCG GCC GGC TTC AAG
633

CAC GGG AAC TGG CAT GAC GTG GGT TTC TGG CAG CTG GAC TTC AGC
678

CTG CCG GTA CCG CCC CGT CCG GTC CTG CCC GTC ACC GAG ATC
723
``` or of a part thereof expressing a polypeptide having plant-protecting capability against Bialaphos.

The invention also relates to any DNA fragment differing from the preferred one indicated hereabove by the replacement of any of its nucleotides by others, yet without modifying the genetic information of the preferred DNA sequence mentioned hereabove (normally within the meaning of the universal genetic code), and furthermore to any equivalent DNA sequence which would encode a polypeptide having the same properties, particularly a Bialaphos-resistance-activity.

It will be understood that the man skilled in the art should be capable of readily assessing those parts of the nucleotide sequences that could be removed from either side of any of the DNA fragments according to the invention, for instance by removing terminal parts on either side of said DNA fragment, such as by an exonucleolytic enzyme, for instance Bal31, by recloning the remaining fragment in a suitable plasmid and by assaying the capacity of the modified plasmid to transform appropriate cells and to protect it against the Bialaphos antibiotic or herbicide as disclosed later, whichever assay is appropriate.

For the easiness of language, these DNA fragments will be termed hereafter as "Bialaphos-resistance DNA". In a similar manner, the corresponding polypeptide will be termed as "Bialaphos-resistance enzyme".

While in the preceding discussion particular emphasis has been put on DNA fragments capable, when introduced into plant cells and plants, to confer on them protection against Bialaphos or PPT, it should be understood that the invention should in no way be deemed as limited thereto.

In a same manner, the invention pertains to DNA fragments which, when introduced into such plant cells, would also confer on them a protection against other GS inhibitors, for instance of intermediate products involved in the natural biosynthesis of phosphinotricin, such as the compounds designated by the abbreviations MP101 (III), MP102 (IV), the formula of which are indicated hereafter:

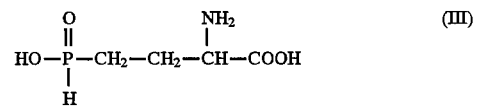

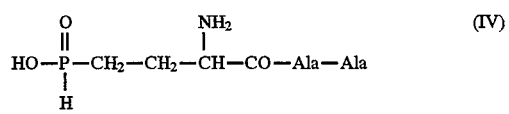

More generally, the invention has opened the route to the production of DNA fragments which, upon proper incorporation into plant cells and plants, can protect them against GS inhibitors when contacted therewith, as this will be shown in a detailed manner in relation to Bialaphos and PPT in the examples which will follow.

This having been established, it will be appreciated that any fragment encoding an enzymatic activity which would protect plant cells and plants against said GS inhibitors, by inactivationg, should be viewed as an equivalent of the preferred fragments which have been disclosed hereabove. This would apply especially to any DNA fragments that would result from genetic screening of the genomic DNAs of strains, particularly of antibiotic-producing strains, likely to possess genes which, even- though structurally different, would encode similar activity with respect to Bialaphos or PPT, or even with respect to other GS inhibitors. This applies to any gene in other strains producing a PPT derivative.

Therefore, it should be understood that the language "Bialaphos-resistance DNA" or "Bialaphos-resistance enzyme" used thereafter as a matter of convenience is intended to relate not only to the DNAs and enzymes specifically concerned with resistance to PPT or most directly related derivatives, but more generally with other DNAs and enzymes which would be capable, under the same circumstances, of inactivating the action in plants of GS inhibitors.

The invention also relates to DNA recombinants containing the above defined Bialaphos-resistance DNA fragments recombined with heterologous DNA, said heterologous DNA containing regulation elements and said Bialaphos-resistance DNA being under the control of said regulation elements in such manner as to be expressible in a foreign cellular environment compatible with said regulation elements. Particularly the abovesaid Bialaphos-resistance-DNA fragments contained in said DNA recombinants are devoid of any DNA region involved in the biosynthesis of Bialaphos, when said Bialaphos-resistance-DNA fragment originate themselves from Bialaphos-producing strains.

By "heterologous DNA" is meant a DNA of an other origin than that from which said Bialaphos-resistance-DNA originated, e.g. is different from that of a *Streptomyces hygroscopicus* or *Streptomyces viridochromogenes* or even more preferably a DNA foreign to Streptomyces DNA. Particularly said regulation elements are those which are capable of controlling the transcription and translation of DNA sequences normally associated with them in said foreign environment. "Cellular" refers both to microorganisms and to cell cultures.

This heterologous DNA may be a bacterial DNA, particularly when it is desired to produce a large amount of the recombinant DNA, such as for amplification purposes. In that respect a preferred heterologous DNA consists of DNA of *E. coli* or of DNA compatible with *E. coli*. It may be DNA of the same origin as that of the cells concerned or other DNA, for instance viral or plasmidic DNA known as capable of replicating in the cells concerned.

Preferred recombinant DNA contains heterologous DNA compatible with plant cells, particularly Ti-plasmid DNA.

Particularly preferred recombinants are those which contain GS inhibitor inactivating DNA under the control of a promoter recognized by plant cells, particularly those plant cells on which inactivation of GS inhibitors is to be conferred.

Preferred recombinants according to the invention further relate to modified vectors, particularly plasmids, containing said GS-inhibitor-inactivating DNA so positioned with respect to regulation elements, including particularly promoter elements, that they enable said GS inhibitor-inactivating DNA to be transcribed and translated in the cellular environment which is compatible with said heterologous DNA. Advantageous vectors are those so engineered as to cause stable incorporation of said GS inhibitor inactivating DNA in foreign cells, particularly in their genomic DNA. Preferred modified vectors are those which enable the stable transformation of plant cells and which confer to the corresponding cells, the capability of inactivating GS inhibitors.

It seems that, as described later, the initiation codon of the Bialaphos-resistance-gene of the *Streptomyces hygroscopicus* strain used herein is a GTG codon. But in preferred recombinant DNAs or vectors, the Bialaphos-resistance-gene is modified by substitution of an ATG initiation codon for the initiation codon GTG, which ATG enables translation initiation in plant cells.

In the example which follows, the plant promoter sequence which has been used was constituted by a promoter of the 35 S cauliflower mosaic virus. Needless to say that the man skilled in the art will be capable of selecting other plant promoters, when more appropriate in relation to the plant species concerned.

According to an other preferred embodiment of the invention, particularly when it is desired to achieve transport of the enzyme encoded by the Bialaphos-resistance-DNA into the chloroplasts, the heterologous DNA fragment is fused to a gene or DNA fragment encoding a transit peptide, said last mentioned fragment being then intercalated between the GS inhibitor inactivating gene and the plant promoter selected.

As concerns means capable of achieving such constructions, reference can be made to the following British applications 84 32757 filed on Dec. 28, 1984 and 85 00336 filed on Jan. 7, 1985 and to the related applications filed in the United-States of America (n°755,173, filed on Jul. 15, 1985), in the European Patent Office (n°85 402596.2, filed on Dec. 20, 1985), in Japan (n°299 730, filed on Dec. 27, 1985), in Israel (n°77 466 filed on Dec. 27, 1985) and in Australia (n°5 165 485, filed on Dec. 24, 1985), all of which are incorporated herein by reference.

Reference can also be made to the scientific literature, particularly to the following articles:

VAN DEN BROECK et al., 1985, Nature, 313, 358–363;
SCHREIER and al., Embo. J., vol. 4, n°1, 25–32.

These articles are also incorporated herein by reference.

For the sake of the record, be it recalled here that under the expression "transit peptide", one refers to a polypeptide fragment which is normally associated with a chloroplast protein or a chloroplast protein sub-unit in a precursor protein encoded by plant cell nuclear DNA. The transit peptide then separates from the chloroplast protein or is proteolitically removed, during the translocation process of the latter protein into the chloroplasts. Examples of suitable transit peptides are those associated with the small subunit of ribulose-1,5 biphosphate (RuBP) carboxylase or that associated with the chlorophyl a/b binding proteins.

There is thus provided DNA fragments and DNA recombinants which are suitable for use in the process defined hereafter.

More particularly the invention also relates to a process, which can be generally defined as a process for producing plants and reproduction material of said plants including a heterologous genetic material stably integrated therein and capable of being expressed in said plants or reproduction material in the form of a protein capable of inactivating or neutralizing the activity of a glutamine synthetase-inhibitor, comprising the non biological steps of producing plants cells or plant tissue including said heterologous genetic material from starting plant cells or plant tissue not able to express that inhibiting or neutralizing activity, regenerating plants or reproduction material of said plants or both from said plant cells or plant tissue including said genetic material and, optionally, biologically replicating said last mentioned plants or reproduction material or both, wherein said non-biological steps of producing said plant cells or plant tissue including said heterologous genetic material, comprises transforming said starting plant cells or plant tissue with a DNA-recombinant containing a nucleotide sequence encoding said protein, as well as the regulatory elements selected among those which are capable of enabling the expression of said nucleotide sequence in said plant cells or plant tissue, and to cause the stable integration of said nucleotide sequence in said plant cells and tissue, as well as in the plant and reproduction material processed therefrom throughout generations.

The invention also relates to the cell cultures containing Bialaphos-resistance-DNA, or more generally said GS-inhibitor-inactivating DNA, which cell cultures have the property of being resistant to a composition containing a GS inhibitor, when cultured in a medium containing such composition at dosages which would be destructive for non transformed cells.

The invention concerns more particularly those plant cells or cell cultures in which the Bialaphos-resistance DNA is stably integrated and which remains present over successive generations of said plant cells. Thus the resistance to a GS inhibitor, more particularly Bialaphos or PPT, can also be considered as a way of characterizing the plant cells of this invention.

Optionally one may also resort to hybridization experiments between the genomic DNA obtained from said plant cells with a probe containing a GS inhibitor inactivating DNA sequence.

More generally the invention relates to plant cells, reproduction material, particularly seeds, as well as plants containing a foreign or heterologous DNA fragment stably integrated in their respective genomic DNAs, said fragments being transferred throughout generations of such plant cells, reproduction material, seeds and plants, wherein said DNA fragment encodes a protein inducing a non-variety-specific enzymatic activity capable of inactivating or neutralizing GS inhibitors, particularly Bialaphos and PPT, more particularly to confer on said plant cells, reproduction material, seeds and plants a corresponding non-variety-specific phenotype of resistance to GS inhibitors.

"Non-variety-specific" enzymatic activity or phenotype aims at referring to the fact that they are not characteristic of specific plant genes or species as this will be illustrated in a non-limitative way by the examples which will follow. They are induced in said plant materials by essentially non-biological processes applicable to plants belonging to species normally unrelated with one another and comprising the incorporation into said plant material of heterologous DNA, e.g., bacterial DNA or chemically synthesized DNA, which does not normally occur in said plant material or which normally cannot be incorporated therein by natural breeding processes, and which yet confers a common phenotype (e.g., herbicide resistance) to them.

The invention is of particular advantageous use in processes for protecting field-cultivated plant species against weeds, which processes comprise the step of treating the field with an herbicide, e.g., Bialaphos or PPT in a dosage effective to kill said weeds, wherein the cultivated plant species then contains in their genome a DNA fragment encoding a protein having an enzymatic activity capable of neutralizing or inactivating said GS inhibitor.

By way of illustration only, effective doses for use in the abovesaid process range from about 0.4 to about 1.6 kg/Hectare of Bialaphos or PPT.

There follows now a disclosure of how the preferred DNA fragment described hereabove was isolated starting from the Streptomyces hygroscopicus strain available at the American Type Culture Collection under deposition number ATCC 21 705, by way of exemplification only.

The following disclosure also provides the technique which can be applied to other strains producing compounds with a PPT moiety.

The disclosure will then be completed with the description of the insertion of a preferred DNA fragment conferring to the transformed cells the capability of inactivating Bialaphos and PPT. Thus the Bialaphos-inactivating-DNA fragment designated thereafter by Bialaphos-resistance gene or "sfr" gene, isolated by the above described technique into plasmids which can be used for transforming plant cells and conferring to them a resistance against Bialaphos, also merely by way of example for non-limitative illustration purposes.

The following disclosure is made with reference to the drawings in which:

FIG. 2 shows the nucleotide sequence of a smaller fragment obtained from pBG1, subcloned into another plasmid (pBG39) and containing the resistance gene;

FIG. 5A shows a determined fragment of the nucleotide sequence of the plasmid obtained in FIG. 3;

FIG. 5B shows the reconstruction of the first codons of a Bialaphos-resistance gene, from a FokI/BglII fragment obtained from pBO39 and the substitution of an ATG initiation codon for the GTG initiation codon of the natural "sfr" gene;

FIG. 5C shows the reconstruction of the entire "sfr" gene, namely the last codons thereof, and its insertion into a plasmid obtained in FIGS. 4A and 4B;

FIG. 8 to 11 will be referred to hereafter.

The following experiment was set up to isolate a Bialaphos-resistance-gene from *S. hygroscopicus*, according to standard techniques for cloning into Streptomyces.

Figure 1:
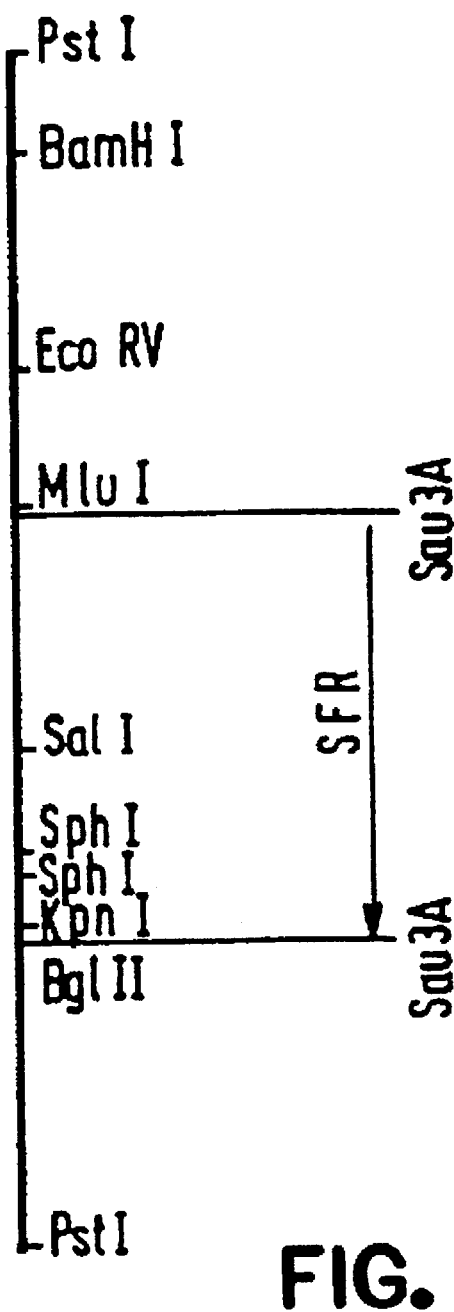
FIG. 1 is a restriction map of a plasmid containing a *Streptomyces hygroscopicus* DNA fragment encoding Bialaphos-resistance, which plasmid, designated hereafter as pBG1 has been constructed according to the disclosure which follows.

2.5 µg of *S. hygroscopicus* genomic DNA and 0.5 µg of Streptomyces vector pIJ61 were cleaved with PstI according to the method described in ref. 6. The vector fragments and genomic fragments were mixed and ligated (4 hours at 10° C. followed by 72 hours at 4° C. in ligation salts which contain 66 mM Tris-HCl (pH 7.5), 1 mM EDTA, 10 mM $MgCl_2$, 10 mM 2-mercaptoethanol and 0.1 mM ATP) at a total DNA concentration of 40 µg $ml^{-1}$ with T4 DNA ligase. Ligation products were introduced into $3\times10^9$ *S. lividans* strain 66 protoplasts by a transformation procedure mediated by polyethylene-glycol (PEG) as described hereafter. These protoplasts gave rise to $5\times10^7$ colonies and $4\times10^4$ pocks after regeneration on 20 plates of R2 agar containing 0.5% of Difco yeast extract (R2 YE). Preparation and composition of the different mediums and buffers used in the disclosed experiments are described hereinafter. When these lawns were replica-plated on minimal medium plates containing 50 µg $ml^{-1}$ Bialaphos, drug resistant colonies appeared at a frequency of 1 per $10^4$ transformants. After purification of the drug resistant colonies, there plasmid DNA was isolated and used to retransform S. lividans protoplasts. Non selective regeneration followed by replication to Bialaphos-containing-medium demonstrated a 100% correlation between pocks and Bialaphos resistant growth. The recombinant plasmids of several resistant clones all contained a 1.7 Kb PstI insert (see FIG. 1).

Subcloning of the Herbicide Resistance Gene

The 1.7 Kb PstI insert was then subcloned into the high copy number streptomycete vector pIJ385 to generate plasmid pBG20. S. lividans strains which contained pBG20 were more than 500 times more resistant to Bialaphos. S. lividans growth is normally inhibited in minimal medium containing 1 µg/ml Bialaphos; growth of transformants containing pBG20 was not noticeably inhibited in a medium containing 500 µg/ml Bialaphos. The PstI fragment was also subcloned in either orientation into the PstI site of the plasmid pBR322, to produce plasmids pBG1 and pBG2, according to their orientation. A test on minimal M9 medium demonstrated that E. coli E8767 containing pBG1 or pBG2 was resistant to Bialaphos.

A ±1.65 Kb PstI—BamHI fragment was subcloned from pBG1 into the plasmid pUC19 to produce the plasmid pBG39, and conferred Bialaphos resistance to E. coli, W3110, C600 and JM83.

Using an in vitro coupled transcription-translation system (ref. 5) from S. lividans extracts, the 1,65 KbPstI—BamHI fragment in pBG39 was shown to direct the synthesis of a 22 Kd protein. In the following, this 1,65 Kb insert includes a fragment coding for a 22 Kd protein and will be called "sfr" gene.

Fine Mapping and Sequencing of the Gene

A 625 bp Sau3A fragment was subcloned from pBG39 into pUC19 and still conferred Bialaphos resistance to a E. coli W3110 host. The resulting clones were pBG93 and pBG94, according to the orientation.

The orientation of the gene in the Sau3A fragment was indicated by experiments which have shown that Bialaphos resistance could be induced with IPTG from the pUC19 lac promoter in pBG93. In the presence of IPTG (0.5 mM) the resistance of pBG93/W3110 increased from 5 to 50 µg/ml on a M9 medium containing Bialaphos. The W3110 host devoid of pBG93, did not grow on M9 medium containing 5 µg/ml Bialaphos. These experiments demonstrated that the Sau3A fragment could be subcloned without loss of activity. They also provided for the proper orientation as shown in the FIG. 2, enclosed thereafter. The protein encoded by these clones was detected by using coupled transcription-translation systems derived from extracts of S. lividans (ref. 7). Depending on the orientation of the Sau3A fragment, translation products of different sizes were observed; 22 Kd for pBG94 and ±28 Kd for pBG93. This indicated that the Sau3A fragment did not contain the entire resistance gene and that a fusion protein was formed which included a polypeptide sequence resulting from the translation of a pUC9 sequence.

In order to obtain large amounts of the protein, a 1.7 Kb PstI fragment from pBG1 was cloned into the high copy number Streptomycete replicon pIJ385. The obtained plasmid, pBG20, was used to transform S. hygroscopicus. Transformants which contained this plasmid had more than 5 times as much PPT acetylating activity and also had increased amounts of a 22 kd protein on sodium dodecyl-sulfate gels (SDS gels). Furthermore, both the acetyl transferase and the 22 kd protein appeared when the production of Bialaphos begun. The correlation of the in vitro data, kinetics of synthesis, and amplified expression associated with pBG20 transformants strongly implied that this 22 Kd band was the gene product.

The complete nucleotide sequence of the 625 bp Sau3A fragment was determined as well as of flanking sequences. Computer analysis revealed the presence of an open reading frame over the entire length of the Sau3A fragment.

Characterization of the sfr Gene Product

A series of experiments were performed to determine that the open reading frame of the "sfr" gene indeed encoded the Bialaphos resistance enzyme. To determine the 5' end of the resistance gene, the $NH_2$-terminal sequence of the enzyme was determined. As concerns more particularly the technique used to determine the said sequence, reference is made to the technique developed by J. VANDEKERCKHOVE, Eur. J. Bioc. 152, p. 9–19, 1985, and to French patent applications n° 85 14579 filed on Oct. 1st, 1985 and n°85 13046 filed on Sep. 2nd, 1985, all of which are incorporated herein by reference.

This technique allows the immobilization on glass fibre sheets coated with the polyquaternary amine commercially available under the registered trademark POLYBRENE of proteins and of nucleic acids previously separated on a sodium dodecylsulfate containing polyacrylamide gel. The transfer is carried out essentially as for the protein blotting on nitrocellulose membranes (ref. 8). This allows the determination of amino-acid composition and partial sequence of the immobilized proteins. The portion of the sheet carrying the immobilized 22 kd protein produced by S. hygroscopicus pBG20 was cut out and the disc was mounted in the reaction chambre of a gas-phase sequenator to subject the glass-fibre bound 22 Kd protein to the Edman degradation procedure. The following amino-acid sequence was obtained:

Pro-Glu-Arg-Arg-Pro-Ala-Asp-Ile-Arg-Arg

This sequence matched an amino-acid sequence which was deduced from the open reading frame of the 625 bp Sau3A fragment. It corresponded to the stretch from codon 3 to codon 12.

Thus, the $NH_2$-terminus of the 22 Kd protein was upstream of this sequence. It was determined that translation of the actual protein was likely to be initiated 2 amino-acids earlier at a GTG initiation codon. GTG is often used as initiator codon in Streptomyces and translated as methionine. The protein translated from the GTG initiation codon would be 183 amino-acids long and would have a molecular weight of 20 550. This was in good agreement with the observed approximate molecular weight of 22 000.

Furthermore, the termination codon, TGA, was located just downstream of the Sau3A site. Cloning of the 625 bp Sau3A fragment in a BamHI site digested pUC19 did not result in the reconstruction of the termination codon. This explained the fusion proteins which were observed in the in vitro transcription-translation analysis.

Mechanism of PPT-resistance

Having defined a first phenotype and some of the physical characteristics of the resistance gene and its gene product, a series of experiments was then carried out to understand the mechanism by which it confers resistance. As described hereabove, PPT is the portion of Bialaphos which inhibits glutamine synthetase (GS) and that N-acetyl PPT is not an inhibitor. Using a standard assay (ref. 9), S. hygroscopicus ATCC 21 705 derivates were shown to contain a PPT acetyl transferase which was not found in S. lividans. The activity does not acetylate the Bialaphos tripepride. *S. lividans* carrying the resistance gene cloned in pBG20 or pBG16 (a plasmid containing the 625 bp Sau3A fragment cloned into another streptomycete vector, pIJ680) also contained the activity which could acetylate PPT but not Bialaphos. The PPT derived reaction product produced by extracts of pBG20/ *S. lividans* was isolated in order to confirm that it was indeed acetyl-PPT. Analysis by mass spectroscopy showed that the molecular weight had increased relative to PPT by the equivalent of one acetyl group. It was thus concluded that the 625 bpSau3A fragment contained sequences which code for PPT acetyl transferase.

The experimental conditions and reagents used in the techniques disclosed hereabove were as follows:

Preparation and Composition of the Mediums and Buffers Above Used

1* P medium: 10.3 g of sucrose, 0.025 g of $K_2SO_4$, 0.203 g of $MgCl_2.6H_2O$ and 0.2 ml of a trace element solution are dissolved in 80 ml of distilled water and auto-claved. Then in order, 1 ml of $KH_2PO_4$ (0.5%), 10 ml of $CaCl_2, 2H_2O$ (3.68%), and 10 ml of TES buffer (0.25M), pH: 7.2) are added. Trace element solution (per liter): $ZnCl_2$, 40 mg; $FeCl_3.6H_2O$, 200 mg; $CuCl_2.2H_2O$, 10 mg; $MnCl_2.4H_2O$, 10 mg; $Na_2B_4O_7.10H_2O$, 10 mg; $(NH_4)_6Mo_7O_{24}.4H_2O$, 10 mg.

2* R2YE: 10.3 g of sucrose, 0.025 g of $K_2SO_4$, 1.012 g of $MgCl_2.6H_2O$, 1 g of glucose, 0.01 g of Difco casamino acids, and 2.2 g of Difco agar are dissolved in 80 ml distilled water and autoclaved. 0.2 ml of trace element solution, 1 ml of $KH_2PO_4$ (0.5%), 8.02 ml of $CaCl_2.2H_2O$ (3.68%), 1.5 ml of L-proline (20%), 10 ml of TES buffer (0.25M) (pH: 7.2), 0.5 ml of (1M) NaOH, 5 ml of yeast extract (10%) are sequentially added.

3* TE: 10 mM TRIS HCl, 1 mM EDTA, pH 8.0.

4* YEME: Difco yeast extract (0.3%), Difco peptone (0.5%), oxoid malt extract (0.3%), glucose (1%).

Transformation of *S. lividans* Protoblasts

1. A culture composed of 25 ml YEME, 34% sucrose, 0.005M $MgCl_2$, 0.5% glycine, in a 250 ml baffled flask, is centrifuged during 30 to 36 hours.

2. The pellet is suspended in 10.3% sucrose and centrifuged. This washing is repeated once.

3. The mycelium is suspended in 4 ml lysozyme solution (1 mg/ml in P medium with $CaCl_2$ and $MgCl_2$ concentrations reduced to 0.0025M) and incubated at 30° C. for 15 to 60 minutes.

4. The solution is mixed by pipetting three times in a 5 ml pipette and incubated for further 15 minutes. 5. P medium (5 ml) is added and mixed by pipetting as in step 4.

6. The solution is filtered through cotton wool and protoplasts are gently sedimented in a bench centrifuge at 800×G during 7 minutes.

7. Protoplasts are suspended in 4 ml P medium and centrifuged again.

8. Step 7 is repeated and protoplasts are suspended in the drop of P medium left after pouring off the supernatant (for transformation).

9. DNA is added in less than 20 µl TE. 10. 0.5 ml PEG 1 000 solution (2.5 g PEG dissolved in 7.5 ml of 2.5% sucrose, 0.0014 $K_2SO_4$, 0.1M $CaCl_2$, 0.05M TRIS-maleic acid, pH 8.0, plus trace elements) is immediately added and pipetted once to mix the components.

11. After 60 seconds, 5 ml of P medium are added and the protoplasts are sedimented by gentle centrifugation.

12. The pellet is suspended in P medium (1 ml).

13. 0.1 ml is plated out on R2YE plates (for transformation dry plates to 85% of their fresh weigh e.g. in a laminar flow cabinet).

14. Incubation at 30° C.

A—Construction of a "sfr" Gene Cassette

A "sfr" gene cassette was constructed to allow subsequent cloning in plant expression vectors.

Isolation of a FokI-BglII fragment from the plasmid pBG39 containing a "sfr" gene fragment led to the loss of the first codons, including the initiation codon, and of the last codons, including the stop codon.

This fragment of the "sfr" gene could be reconstructed in vitro with synthetic oligonucleotides which encode appropriate amino-acids.

The complementary synthetic oligonucleotides were 5'-CATGAGCCCAGAAC and 3'-TCGGGTCTTGCTGC.

By using such synthetic oligonucleotides, the 5' end of the "sfr" gene could be reformed and the GTG initiation codon substituted for a codon well translated by plant cells, particularly an ATG codon.

The DNA fragment containing the oligonucleotides linked to the "sfr" gene was then inserted into an appropriate plasmid, which contained a determined nucleotide sequence thereafter designated by an "adapter" fragment.

This adapter fragment comprised:

a TGA termination codon which enabled the last codons of the "sfr" gene to be reformed;

appropriate restriction sites which enabled the insertion of the fragment of the nucleotide sequence comprising the "sfr" gene partially reformed with the synthetic oligonucleotides; this insertion resulted in the reconstruction of an intact "sfr" gene;

appropriate restriction sites for the isolation of the entire "sfr" gene.

The "sfr" gene was then inserted into another plasmid, which contained a suitable plant promoter sequence. The plant promoter sequence consisted of the cauliflower mosaic virus promoter sequence (p35S). Of course the invention is not limited to the use of this particular promoter. Other sequences could be chosen as promoters suitable in plants, for example the TR 1'-2' promoter region and the promoter fragment of a Rubisco small subunit gene from *Arabidopsis thaliana* hereafter described.

Figure 3:
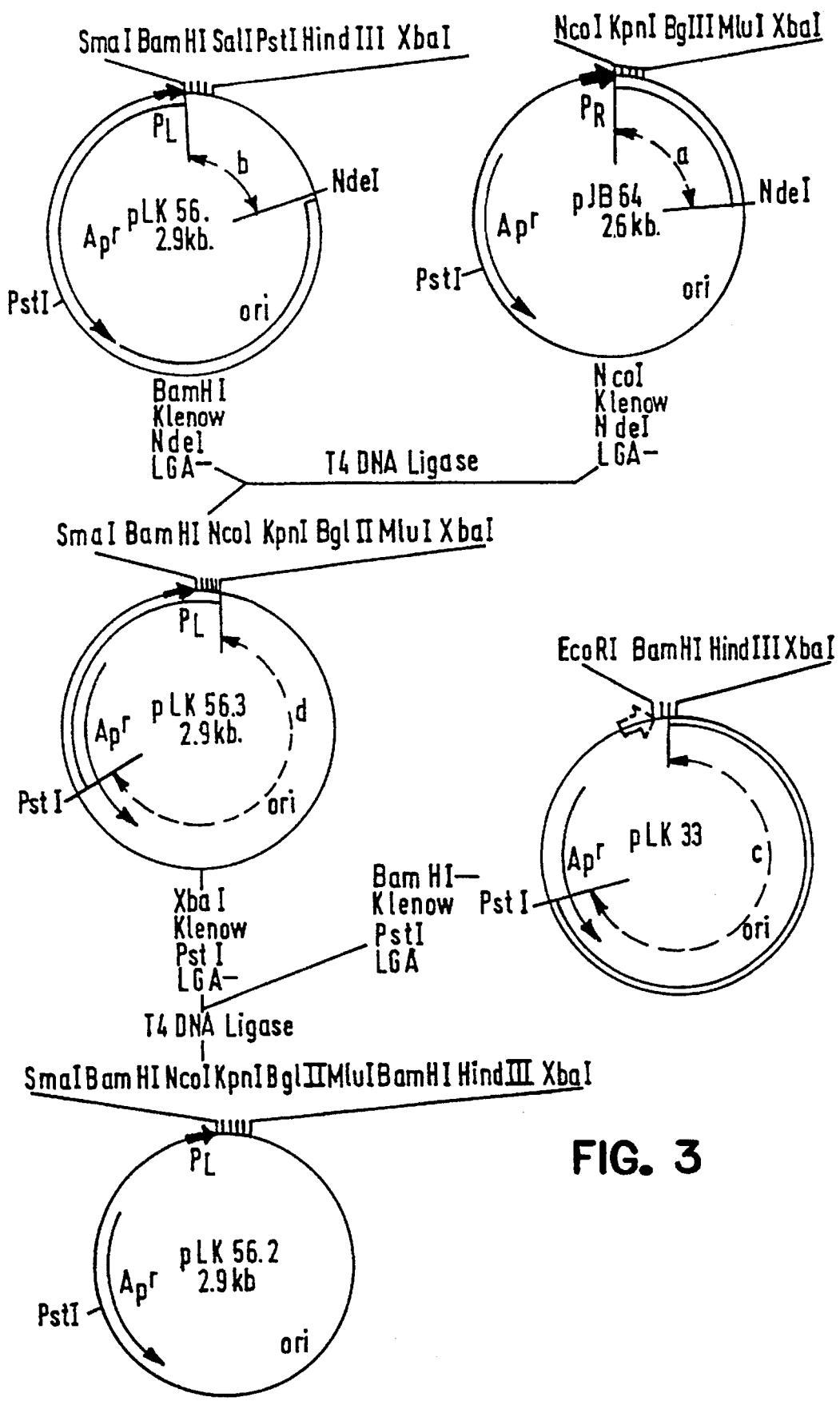
FIG. 3 shows the construction of a series of plasmids given by way of example, which plasmids aim at providing suitable adaptation means for the insertion therein of the Bialaphos-resistance gene or "sfr" gene.

1* Construction of the Plasmid pLK56.2 (FIG. 3)

The construction of plasmid pLK56.2 aimed at obtaining a suitable adaptor including the following sequence of restriction sites: SmaI, BamHI, NcoI, KpnI, BglII, MluI, BamHI, HindIII and XbaI.

The starting plasmids used for this construction, pLK56, pJB64 and pLK33 were those disclosed by BOTTERMAN (ref. 11).

The DNA fragments hereafter described were isolated and separated from low melting point agarose (LGA).

The plasmid pLK56 was cleaved by the enzymes BamHI and NdeI. A NcoI-NdeI fragment (referred to in the drawings by arc "a" in broken line) obtained from plasmid pJB64 was substituted in pLK56 for the BamHI-NdeI fragment shown at "b". Ligation was possible after filling in the BamHI and NcoI protruding ends with the DNA polymerase I of E. coli (Klenow's fragment).

Particularly recircularization took place by means of a T4 DNA ligase. A new plasmid pLK56.3 was obtained.

This plasmid was cleaved by the enzymes XbaI and PstI.

The BamHI-PstI fragment of pLK33 (c) (on FIG. 3) was substituted for the XbaI-PstI fragment (d) of pLK56.3, after repairing of their respective ends by Klenow's fragment.

After recircularization by means of the T4 DNA ligase, the obtained plasmid pLK56.2 contained a nucleotide sequence which comprised the necessary restriction sites for the subsequent insertion of the "sfr" gene.

Figure 4A:
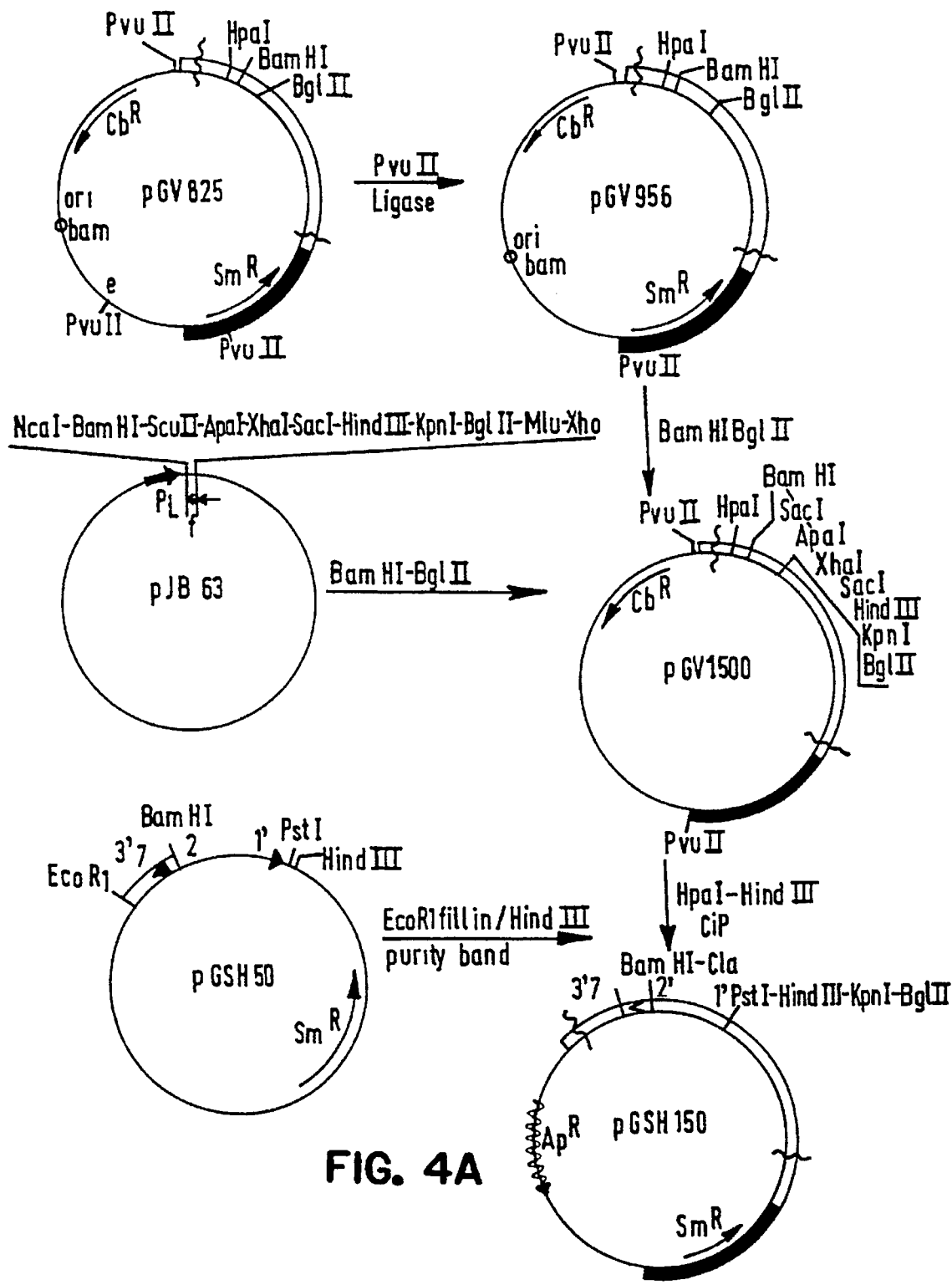
FIG. 4A and 4B show the construction of a series of plasmids given by way of example, which plasmids contain suitable plant cell promoter sequences able to initiate transcription and expression of the foreign gene inserted under their control into said plasmids.

2° Construction of the Plasmid pGSH150 (FIG. 4A)

Parallel with the last discussed construction, there was produced a plasmid containing a promoter sequence recognized by the polymerases of plant cells and including suitable restriction sites, downstream of said promoter sequence in the direction of transcription, which restriction sites are then intented to enable the accomodation of the "sfr" gene then obtainable from pLK56.2, under the control of said plant promoter.

Plasmid pGV825 is described in DEBLAERE et al. (ref. 10). Plasmid pJB63 is from BOTTERMAN (ref. 11).

pGV825 was linearized with PvuII and recircularized by the T4 DNA ligase, resulting in the deletion of an internal PvuII fragment shown at (e), (plasmid pGV956).

pGV956 was then cleaved by BamHI and BglII.

The BamHI-BglII fragment (f) obtained from pJB63 was dephosphorylated with calf intestine phosphatase (CIP) and substituted for the BamHI-BglII fragment of pGV956.

Plasmid pGV1500 was obtained after recircularization by means of T4 DNA ligase.

An EcoRI-HindIII fragment obtained from plasmid pGSH50 was purified. The latter plasmid carried the dual TR 1'-2' promoter fragment described in VELTEN et al., (ref. 13). This fragment was inserted in pGV1500, digested with HpaI and HindIII and yielded pGSH150.

This plasmid contains the promoter fragment in front of the 3' end of the T-DNA transcript 7 and a BamHI and ClaI sites for cloning.

Figure 4B:
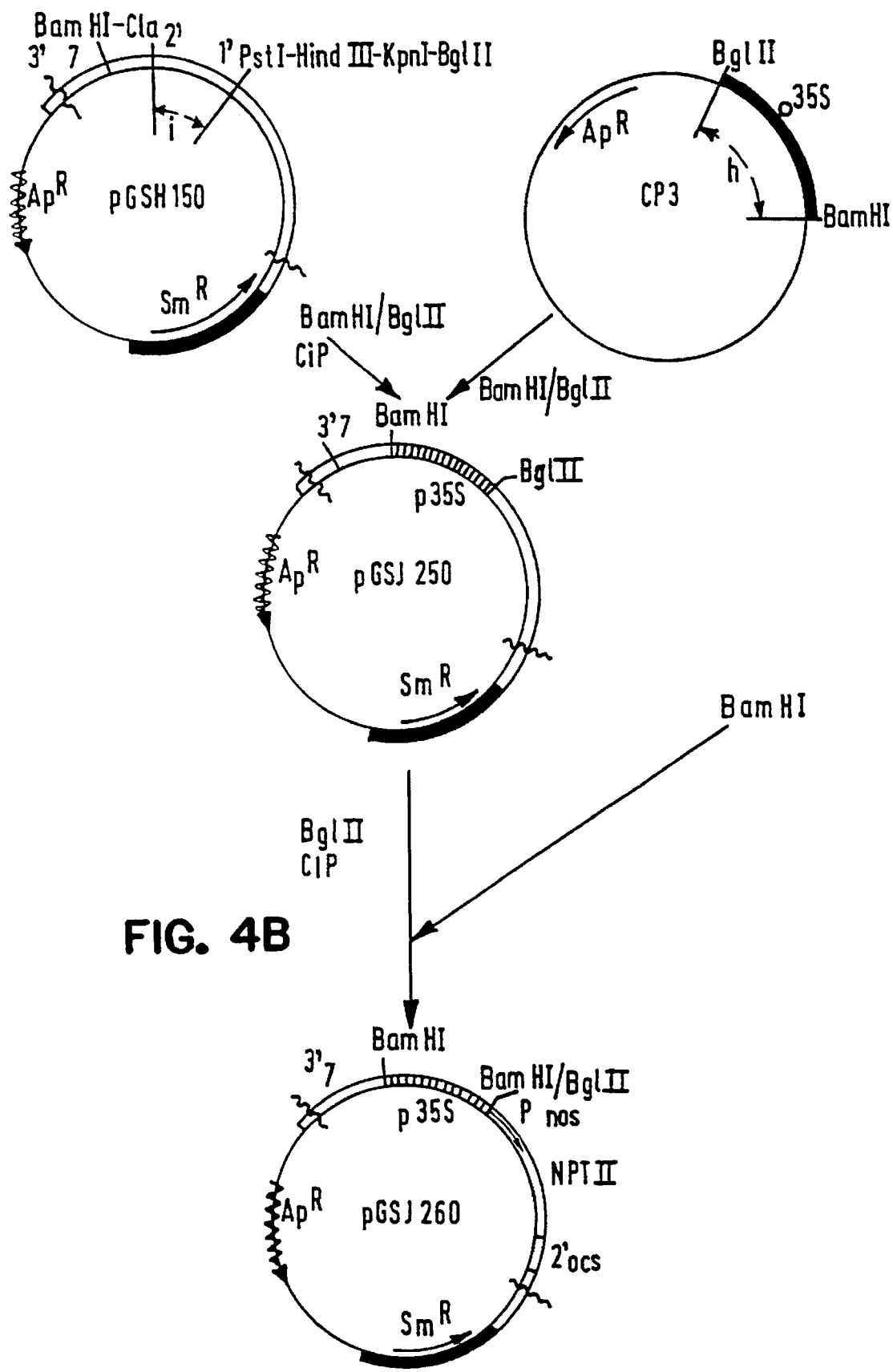

3° Construction of the Plasmid pGSJ260 (FIG. 4B)

CP3 is a plasmid derived from pBR322 and which contains the 35S promoter region of cauliflower mosaic virus within a BamHI fragment.

pGSH150 was cut by BamHI and BglII.

The BamHI-BglII fragment (h) of CP3, which contained the nucleotide sequence of p35S promoter, was substituted for the BamHI-BglII fragment (i) in pGSH150 to form plasmid pGSJ250. pGSJ250 was then opened at its BglII restriction site.

A BamHI fragment obtained from mGV2 (ref. 12) was inserted in pGSJ250 at the BglII site to form plasmid pGSJ260.

However prior to inserting the "sfr" gene obtainable from pLK56.2 into plasmid pGSJ260, it was still desirable to further modify the first in order to permit insertion in a more practical manner. Thus pLK56.2 was further modified as discussed below to yield pGSR1.

Starting from plasmid pGSJ260, two plasmid constructions for subsequent transformations of plant cells were made:

a first plasmid permitting the expression of the "sfr" gene in the cytoplasm of plant cells, and a second plasmid so modified as to achieve transport of the Bialaphos-resistance enzymes to the chloroplasts of plant cells.

First case: plasmid enabling the expression of the "sfr" gene in the cytoplasm of plant cells Cloning of the sfr gene cassette in a plant expression vector (pGSR2) (FIG. 5)

On FIG. 5A, the nucleotide sequence of the adapter of pLK56.2 is shown. In particular, the locations of BamHI, NcoI, BglII restriction sites are shown.

This adapter fragment was cleaved by the enzymes NcoI and BglII.

FIG. 5B shows the FokI-BglII fragment (j) obtained from pBG39. The locations of these two restriction sites are shown on FIG. 2.

Using synthetic oligonucleotides, the first codons of the "sfr" gene were reformed, particularly the 5' end of the gene in which a ATG initiation codon was substituted for the initial GTG codon.

This FokI-BglII fragment completed with the synthetic oligonucleotides was then substituted in pLK56.2 for the NcoI-BglII fragment of the adapter. The 3' end of the gene was thus reformed too, after recircularization with T4 DNA ligased. The plasmid obtained, pGSR1, thus contained the entire "sfr" gene inserted in its adapter.

The plasmid pGSJ260 was then opened by BamHI (FIG. 5C) and the BamHI fragment obtained from pGSR1, which contained the entire "sfr" gene, was inserted into pGSJ260.

Figure 6A:
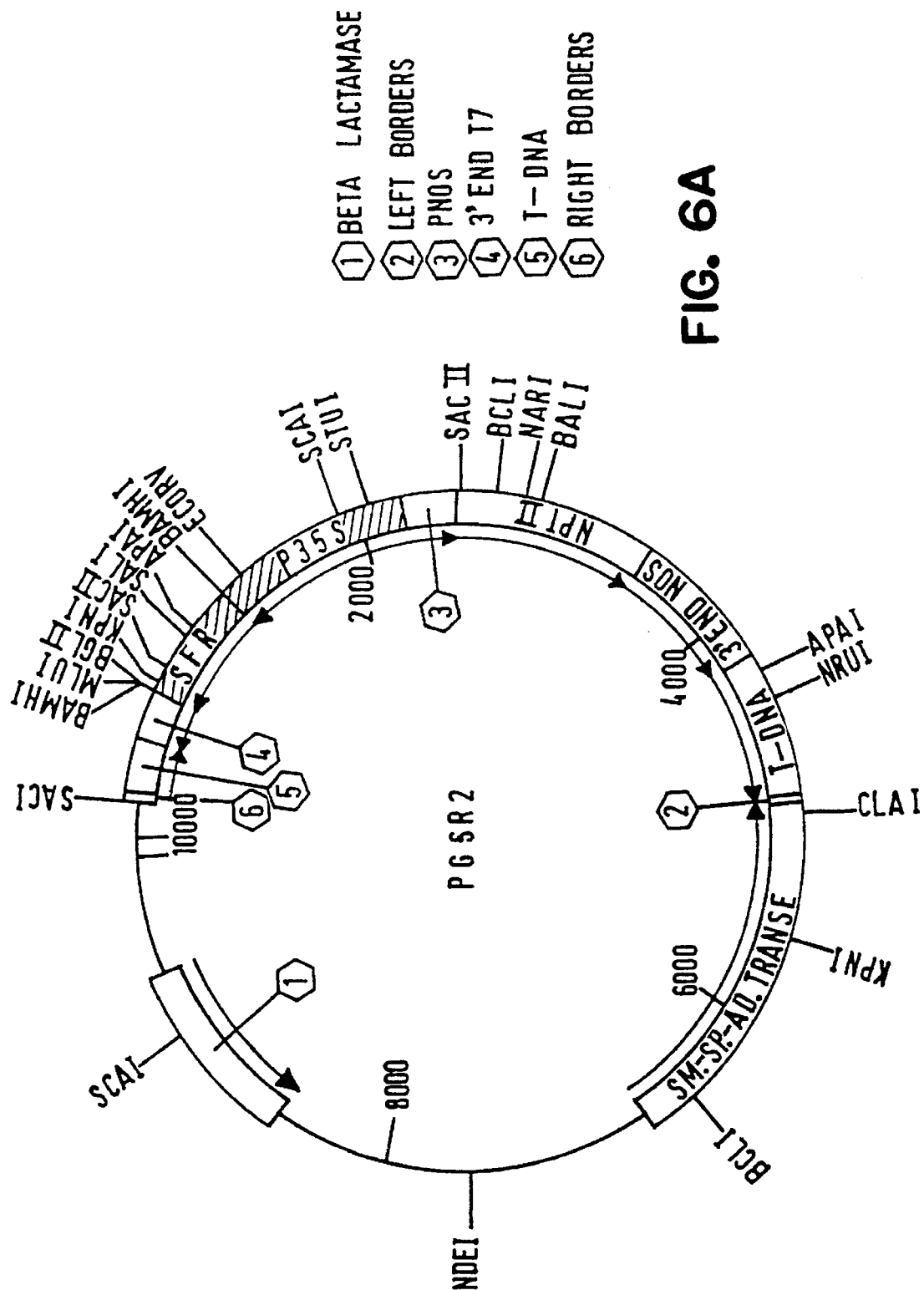
FIG. 6A shows an expression vector containing the "sfr" gene placed under the control of a plant cell promoter.

The obtained plasmid, pGSR2 (see FIG. 6A) contained a pBR322 replicon, a bacterial streptomycin resistance gene (SDM-SP-AD-transferase) and an engineered T-DNA consisting of:

the border fragments of the T-DNA;

a chimeric kanamycin gene which provided a dominant selectable marker in plant cells; and a chimeric "sfr" gene.

The chimeric "sfr" gene consisting of:

the promoter region of the cauliflower mosaic virus (p35S);

the "sfr" gene cassette as described in FIG. 5;

the 3' untranslated region, including the polyadenylation signal of T-DNA transcript 7.

pGSR2 was introduced into Agrobacterium tumefaciens recipient C58ClRif$^R$ (pUV2260) according to the procedure described by DEBLAERE et al. (ref. 10).

This strain was used to introduce the chimeric "sfr" gene in N. tabacum SR$_1$ plants.

Two variant plasmids deriving from pGSR2, namely pGSFR280 and pGSFR281, have been constructed. They differ in the untranslated sequence following the transcription initiation site. In pGSR2, this fragment consists of the following sequence:

GAGGACACGCTGAAATCACCAGTCTCG-GATCCATG;

while it consists of:

GAGGACACGCTGAAATCACCAGTCTCTC-TACAAATCGATCCATG in pGSR280 and of

Figure 6B:
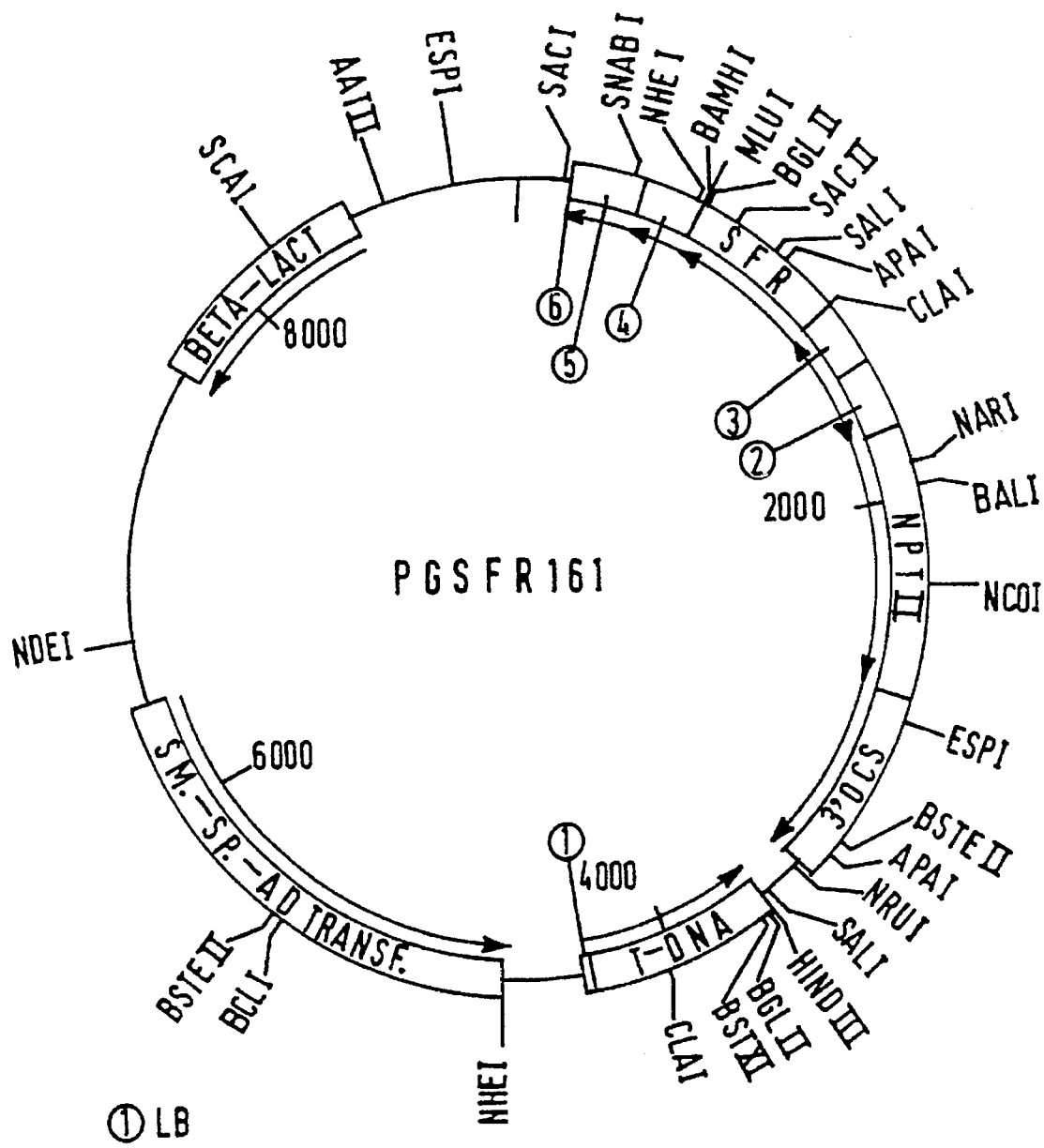
FIG. 6B shows another expression vector deriving from the one shown in FIG. 6A, by the substitution of some nucleotides.

GAGGACACGCTGAAATCACCAGTCTCTC-TACAAATCGATG in pGSFR281, with an ATG codon being the initiation codon of the "sfr" gene. The "sfr" gene is also fused to the TR1'-2' promoter in the plasmid pGSH150 (FIG. 4A) yielding pGSFR160 and pGSFR161 (FIG. 6B). These plasmids contain slight differences in the pTR2 "sfr" gene configuration: the "sfr" gene is correctly fused to the endogenous gene 2' ATG in pGSFR161 (for sequences see ref. 13), whereas 4 extra base pairs (ATCC) are present just ahead of the ATG codon in pGSFR160. Otherwise, plasmids p65FR161 and p65FR160 are completely identical.

All plasmids are introduced in Agrobacterium by cointegration in the acceptor plamids pGV2260 yielding the respective plasmids pGSFR1280, pGSFR1281, pGSFR1160 and pGSFR1161.

Second case; construction of a plasmid containing the "sfr" gene downstream of a DNA sequence encoding a transit peptide and suitable for achieving subsequent translocation of the "sfr" gene expression product into plant-cell-chloroplasts In another set of experiments, the nucleotide sequence which contained the "sfr" gene was fused to a DNA sequence encoding a transit peptide so as to enable its transport into chloroplasts.

A fragment of the "sfr" gene was isolated from the adapter fragment above described and fused to a transit peptide. With synthetic oligonucleotides, the entire "sfr" gene was reconstructed and fused to a transit peptide.

The plasmid (plasmid pATS3 mentioned below) which contained the nucleotide sequence encoding the transit peptide comprised also the promoter sequence thereof.

Figure 7:
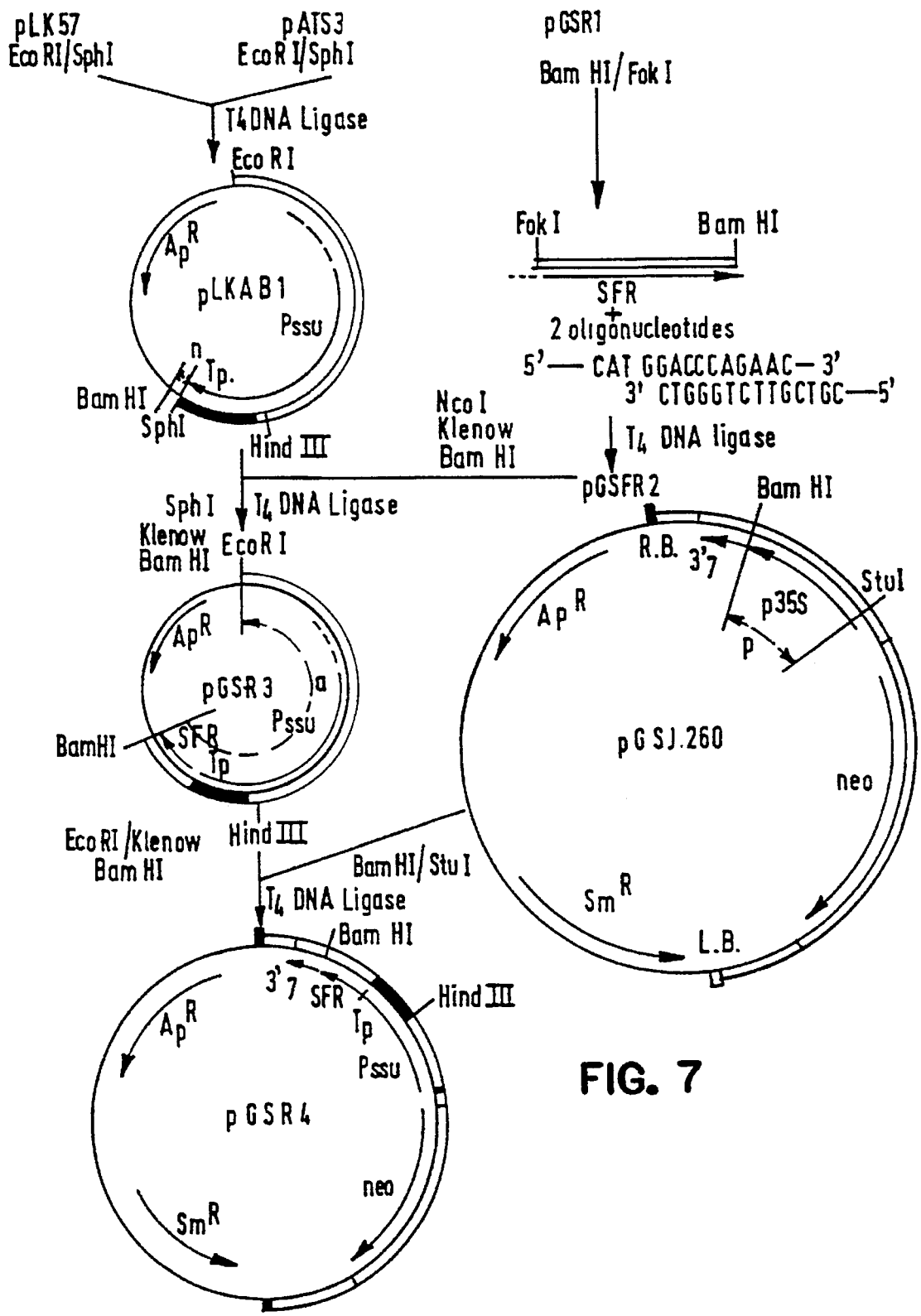
FIG. 7 shows the construction of a series of plasmids given by way of examples, to ultimately produce plasmids containing the promoter region and the transit peptide sequence of a determined plant cell gene, for the insertion of the "sfr" gene under the control of said promoter region and downstream of said transit peptide sequence.

Construction of the plasmid pGSR4 which contains the "sfr" gene fused to a DNA sequence encoding transit peptide (FIG. 7)

Plasmid pLK57 is from BOTTERMAN, (ref. 11). Plasmid pATS3 is a pUC19 clone which contains a 2 Kb EcoRI genomic DNA fragment from *Arabidopsis thaliana* comprising the promoter region and the transit peptide nucleotide sequence of the gene, the expression thereof is the small subunit of ribulose biphosphate carboxylase (ssu). The *A. thaliana* small subunit was isolated as a 1 500 bp EcoRI-SphI fragment. The SphI cleavage site exactly occurs at the site where the coding region of the mature ssu protein starts.

Plasmids pLK57 and pATS3 were opened with EcoRI and SphI. After recircularization by means of the T4 DNA ligase, a recombinant plasmid pLKAB1 containing the sequence encoding the transit peptide (Tp) and its promoter region (Pssu) was obtained.

In order to correctly fuse the "sfr" gene at the cleavage site of the signal peptide, the N-terminal gene sequence was first modified. Since it was observed that N-terminal gene fusions with the "sfr" gene retain their enzymatic activity, the second codon (AGC) was modified to a GAC, yielding an NcoI site overlapping with the ATG initiator site. A new plasmid, pGSSFR2 was obtained. It only differs from pGSR1 (FIG. 5B), by that mutation. The NcoI-BamHI fragment obtained from pGSFR2 was fused at the SphI end of the transit peptide sequence. In parallel, the "sfr" gene fragment was fused correctly to the ATG initiator of the ssu gene (not shown in figures).

Introduction of the "sfr" Gene into a Different Plant Species

The Bialaphos-resistance induced in plants by the expression of chimeric genes, when the latter have been transformed with appropriate vectors containing said chimeric genes, has been demonstrated as follows. The recombinant plasmids containing the "sfr" gene were introduced separately by mobilization into Agrobacterium strain C58C$_1$ Rif$^R$ (pGV2260) according to the procedure described by DEBLAERE and al., Nucl. Acid. Res., 13, p. 1 477, 1985. Recombinant strains containing hybrid Ti plasmides were formed. These strains were used to infect and transform leaf discs of different plant species, according to a method essentially as described by HORSH and al., 1985, Science, vol. 227. Transformation procedure of these different plant species given by way of example, is described thereafter.

1. Leaf disc transformation of *Nicotiana tabacum*
Used Media are described thereafter:

| | |
|---|---|
| $A_1$ MS salt/2 | + 1% sucrose |
| | 0.8% agar |
| | pH 5.7 |
| $A_{10}$ B5-medium | + 250 mg/l NH$_4$NO$_3$ |
| | 750 mg/l CaCl$_2$ 2H$_2$O |
| | 0.5 g/l 2-(N-Morpholino)ethane- |
| | sulfonic acid (MES) pH 5.7 |
| | 30 g/l sucrose |
| $A_{11}$ B5-medium | + 250 mg/l NH$_4$NO$_3$ |
| | 0.5 g/l MES pH 5.7 |
| | 2% glucose |
| | 0.8% agar |
| | 40 mg/l adenine |
| | + 1 mg/l 6-Benzylaminopurine (BAP) |
| | 0.1 mg/l Indole-3-acetic acid (IAA) |
| | 500 mg/l Claforan |
| $A_{12}$ B5-medium | + 250 mg/l NH$_4$NO$_3$ |
| | 0.5 g/l MES pH 5.7 |
| | 2% glucose |
| | 0.8% agar |
| | 40 mg/l adenine |
| | + 1 mg/l BAP |
| | 200 mg/l claforan |
| $A_{13}$ MS-salt/2 | + 3% sucrose |
| | 0.5 MES g/l pH 5.7 |
| | 0.7% agar |
| | 200 mg/l claforan |
| Bacterial medium = min A: | (Miller 1972) 60 mM K$_2$HPO$_4$, 3H$_2$O, |
| | 33 mM KH$_2$PO$_4$; 7.5 mM (NH$_4$)$_2$SO4 |
| | 1.7 M trinatriumcitrat; 1 mM MgSO$_4$; |
| | 2 g/l glucose; 50 mg/l vitamine B1 |

Plant Material

Nicotiana tabacum cv. Petit Havana SR1
Plants are used 6 to 8 weeks after subculture on medium $A_1$

Infection midribs and edges are removed from leaves.

Remaining parts are cut into segments of about 0.25 cm$^2$ and are placed in the infection medium $A_{10}$ (about 12 segments in a 9 cm Petri dish containing 10 ml $A_{10}$).

Segments are then infected with 25 μl per Petri dish of a late log culture of the Agrobacterium strain grown in min A medium.

Petri dish are incubated for 2 to 3 days at low light intensity.

After 2 to 3 days medium is removed and replaced by 20 ml of medium $A_{10}$ containing 500 mg/l clarofan.

Selection and Shoot Induction

The leaf discs are placed on medium $A_{11}$ containing a selective agent:

100 mg/l kanamycin and 10 to 100 mg/l phosphinotricin.

Leaf discs are transferred to fresh medium weekly.

After 3 to 4 weeks regenating calli arise. They are separated and placed on medium $A_{12}$ with the same concentration of selective agent as used for the selection.

Rooting

After 2 to 3 weeks the calli are covered with shoots, which can be isolated and transferred to rooting medium $A_{13}$ (without selection).

Rooting takes 1 to 2 weeks.

After a few more weeks, these plants are propagated on medium $A_1$.

2. Tuber disc infection of *Solanum tuberosum* (potato)

Used media are described thereafter:

| | |
|---|---|
| $C_1$ B5-medium | + 250 mg/l $NH_4NO_3$ |
| | 300 mg/l $(CaCH_2PO_4)_2$ |
| | 0.5 g/l MES pH 5.7 |
| | 0.5 g/l polyvinylpyrrolidone (PVP) |
| | 40 g/l mannitol (=0.22M) |
| | 0.8% agar |
| | 40 mg/l adenine |
| $C_2$ B5-medium | + 250 mg/l $NH_4NO_3$ |
| | 400 mg/l glutamine |
| | 0.5 g/l MES pH 5.7 |
| | 0.5 g/l PVP |
| | 40 g/l mannitol |
| | 40 mg/l adenine |
| | 0.8% agar |
| | + 0.5 mg/l transzeatine |
| | 0.1 mg/l IAA |
| | 500 mg/l clarofan |
| $C_5$ MS salt/2 | + 3% sucrose |
| | 0.7% agar |
| | pH 5.7 |
| $C_7$ B5-medium | + 250 mg/l $NH_4NO_3$ |
| | 400 mg/l glutamine |
| | 0.5 g/l MES pH 5.7 |
| | 0.5 g/l PVP |
| | 20 g/l mannitol |
| | 20 g/l glucose |
| | 40 mg/l adenine |
| | 0.6% agarose |
| | +0.5 mg/l transzeatine |
| | 0.1 mg/l IAA |
| | 500 mg/l clarofan |
| $C_8$ B5-medium | + 250 mg/l $NH_4NO_3$ |
| | 400 mg/l glutamine |
| | 0.5 g/l MES pH 5.7 |
| | 0.5 g/l PVP |
| | 20 g/l mannitol |
| | 20 g/l gluose |
| | 40 mg/l adenine |
| | 0.6% agarose |
| | + 200 mg/l clarofan |
| | 1 mg/l transzeatine |
| $C_9$ B5-medium | + 250 mg/l $NH_4NO_3$ |
| | 400 mg/l glutamine |
| | 0.5 g/l MES pH 5.7 |
| | 0.5 g/l PVP |
| | 20 g/l mannitol |
| | 20 g/l glucose |
| | 40 mg/l adenine |
| | 0.6% agarose |
| | + 1 mg/l transzeatine |
| | 0.01 mg/l Gibberellic acid $A_3$ ($GA)_3$ |
| | 100 mg/l clarofan |
| $C_{11}$ MS salt/2 | + 6% sucrose |
| | 0.7% agar |
| Bacterial medium = min A: | (Miller 1972 60 mM $K_2HPO_4.3H_2O$; 33 mM $KH_2PO_4$; 7.5 mM $(NH_4)_2SO_4$; 1.7 trinatriumcitrat; 1mM $MgSO_4$; 2 g/l glucose; 50 mg/l vitamine B1. |

Plant Material

Tubers of *Solanum tuberosum* c.v Berolina c.v Désirée

Infection

Potatoes are peeled and washed with water.

Then they are washed with concentrated commercial bleach for 20 minutes, and rinsed 3 to 5 times with sterile water.

The outer layer is removed (1 to 1.5 cm)

The central part is cut into discs of about 1 cm² and 2 to 3 mm thick.

Discs are placed on medium $C_1$ (4 pieces in a 9 cm Petri dish).

10 μl of a late log culture of an Agrobacterium strain grown in min A medium is applied on each disc.

Discs are incubated for 2 days at low light intensity.

Selection and Shoot Induction

Discs are dried on a filter paper and transferred to medium $C_2$ with 100 mg/l kanamycin.

After one month small calli are removed from the discs and transferred to medium $C_7$ containing 50 mg/l kanamycin.

After a few more weeks, the calli are transferred to medium $C_8$ containing 50 mg/l kanamycin.

If little shoots start to develop, the calli are transferred to elongation medium $C_9$ containing 50 mg/l Kanamycin.

Rooting

Elongated shoots are separated and transferred to rooting medium $C_{11}$.

Rooted shoots are propagated on medium $C_5$.

3. Leaf disc infection of *Lycopersicum esculentum* (tomato)

Used media are described thereafter

| | |
|---|---|
| $A_1$ MS salt/2 | + 1% sucrose |
| | 0.8% agar |
| | pH 5.7 |
| $B_1$ B5-medium | + 250 mg/l $NH_4NO_3$ |
| | 0.5 g/l MES pH 5.7 |
| | 0.5 g/l PVP |
| | 300 mg/l Ca $(H_2PO_4)_2$ |
| | 2% glucose |
| | 40 mg/l adenine |
| | 40 g/l mannitol |
| $B_2$ B5-medium | + 250 mg/l $NH_4NO_3$ |
| | 0.5 g/l MES pH 5.7 |
| | 0.5 g/l PVP |
| | 400 mg/l glutamine |
| | 2% glucose |
| | 0.6% agarose |
| | 40 mg/l adenine |
| | 40 g/l mannitol |
| | + 0.5 mg/l transzeatine |
| | 0.01 mg/l IAA |
| | 500 mg/l claforan |
| $B_3$ B5-medium | + 250 mg/l $NH_4NO_3$ |
| | 0.5 g/l MES pH 5.7 |
| | 0.5 g/l PVP |
| | 400 mg/l glutamine |
| | 2% glucose |
| | 0.6% agarose |
| | 40 mg/l adenine |
| | 30 g/l mannitol |
| | + 0.5 mg/l transzeatine |
| | 0.01 mg/l IAA |
| | 500 mg/l clarofan |
| $B_4$ B5-medium | + 250 mg/l $NH_4NO_3$ |
| | 0.5 g/l MES pH 5.7 |
| | 0.5 g/l PVP |
| | 400 mg/l glutamine |
| | 2% glucose |
| | 0.6% agarose |
| | 40 mg/l adenine |
| | 20 g/l mannitol |
| | + 0.5 mg/l transzeatine |
| | 0.01 mg/l IAA |

| | |
|---|---|
| B$_5$ B5-medium | 500 mg/l clarofan<br>+ 250 mg/l NH$_4$NO$_3$<br>0.5 g/l MES pH 5.7<br>0.5 g/l PVP<br>400 mg/l glutamine<br>2% glucose<br>0.6% agarose<br>40 mg/l adenine<br>10 g/l mannitol<br>+ 0.5 mg/l transzeatine<br>0.01 mg/l IAA |
| B$_6$ B5-medium | 500 mg/l clarofan<br>+ 250 mg/l NH$_4$NO$_3$<br>0.5 g/l MES pH 5.7<br>0.5 g/l PVP<br>400 mg/l glutamine<br>2% glucose<br>0.6% agarose<br>40 mg/l adenine<br>+ 0.5 mg/l transzeatine<br>0.01 mg/l IAA |
| B$_7$ B5-medium | 200 mg/l clarofan<br>+ 250 mg/l NH$_4$NO$_3$<br>0.5 g/l MES pH 5.7<br>0.5 g/l PVP<br>400 mg/l glutamine<br>2% glucose<br>0.6% agarose<br>40 mg/l adenine<br>+ 1 mg/l transzeatine |
| B$_8$ MS salt/2 | 200 mg/l clarofan<br>+ 2% sucrose<br>0.5 g/l MES pH 5.7<br>0.7% agar |
| B$_9$ B5-medium | + 250 mg/l NH$_4$NO$_3$<br>0.5 g/l MES pH 5.7<br>0.5 g/l PVP<br>2% glucose<br>0.6% agarose<br>40 mg/l adenine<br>+ 1 mg/l transzeatine<br>0.01 mg/l GA$_3$ |
| Bacterial medium = min A: | (Miller 1972) 60 mM<br>K$_2$HPO$_4$.3H$_2$O;<br>33 mM KH$_2$PO$_4$; 7.5 mM(NH$_4$)$_2$SO$_4$;<br>1.7 M trinatriumcitrat; 1 mM<br>MgSO$_4$;<br>2 g/l glucose; 50 mg/l vitamine B1 |

Plant Material

Lycopersicum esculentum cv. Lucullus. Plants are used 6 weeks after subculture on medium A$_1$.

Infection

Midrib is removed from the leaves.

Leaves are cut in segments of about 0.25 to 1 cm$^2$ (the edges of the leaves are not wounded, so that only maximum 3 sides of the leaf pieces is wounded).

Segments are placed in infection medium B$_1$ (upside down), about 10 segments in a 9 cm Petri dish.

Segments are then infected with 20 μl per Petri dish of a late log culture of the *Agrobacterium strain grown in min A medium*.

Petri dishes incubate for 2 days at low light intensity.

Medium is removed after 2 days and replaced by 20 ml of medium B$_1$ containing 500 mg/l clarofan.

Selection and Shoot Induction

The leaf discs are placed in medium B$_2$+50 or 100 mg/l kanamycin.

Each 5 days the osmotic pressure of the medium is lowered by decreasing the mannitol concentration, transfers are done consecutively in medium B$_3$, B$_4$, B$_5$, and B$_6$.

After one month calli with meristems are separated from the leaf discs and placed on medium B$_7$ with 50 or 100 mg/l kanamycin.

Once little shoots have formed, calli are transferred to elongation medium B$_9$ with 50 or 100 mg/l kanamycin.

Rooting

Elongated shoots are separated and transferred to medium B$_8$ for rooting.

Plants are propagated on medium A$_1$.

Greenhouse Tests for Herbicide Resistance Material and Method

In this experiment, two herbicides comprising phosphinotricin as active ingredient, are used.

These compounds are those commercially available under the registered trademarks BASTA$^R$ and MEIJI HERBIACE$^R$.

These products are diluted to 2% with tap water. Spraying is carried out on a square meter area from the four corners. Temperature of the greenhouse is about 22° C. for tobaccos and tomato, and above 10° C. to 15° C. for potato.

Results

Tobacco spraytest a) *Nicotiana tabacum* cv. Petit Havana SR1 plants transformed with the chimeric "sfr" genes as present in pGSFR1161 or pGSFR1281, as well as unstransformed control plants (from 10 cm to 50 cm high) are treated with 20 l BASTA$^R$/ha. Control SR1 plants die after 6 days, while transformed plants are fully resistant to 20 l BASTA$^R$/ha and continue growing undistinguishable from untreated plants. No visible damage is detected, also the treatment is repeated every two weeks. The treatment has no effect in subsequent flowering. The recommended dose oF BASTA$^R$ herbicide in agriculture is 2.5–7.5 l/ha.

b) A similar experiment is performed using 8 l/ha MEIJI HERBIAC$^R$. The transformed plants (the same as above) are fully resistant and continue growing undistinguishable from untreated plants. No visible damage is detectable.

Potato spray test

Untransformed and transformed potato plants (*Solanum tuberosum* cv. Berolina) (20 cm high) with the chimeric "sfr" gene as present in pGSFR1161 or pGSFR1281 are treated with 20 l BASTA$^R$/ha. Control plants die after 6 days while the transformed plants do not show any visible damage. They grow undistiguishable from untreated plants.

tomato spray test

Untransformed and transformed tomato plants (*lvcopersium esculentum* c.v. luculus) (25 cm high) with the chimeric "sfr" gene as present in pGSFR1161 and pGSFR1281 are treated with 20 l BASTA$^R$/ha. control plants die after six days while transformed plants are fully resistant. They do not show any visible damage and grow undistiguishable from untreated plants.

Growth control of phytopathogenic fungi with transformed plants

In another set of experiments, potato plants expressing chimeric "sfr" genes as present in pGSFR1161 or pGSFR1281 are grown in a greenhouse compartment at 20° C. under high humidity. Plants are innoculated by spraying 1 ml of a suspension of 10$^6$ *Phytophtora infestans* spores per ml. Plants grow in growth chambers (20° c., 95% humidity, 4 000 lux) until fungal disease symptoms are visible (one week). One set of the plants are at that moment sprayed with Bialaphos at a dose of 8 l/ha. Two weeks later, untreated plants are completely ingested by the fungus. The growth of the fungus is stopped on the Bialaphos treated plants and no further disease symptoms evolve. The plants are effectively protected by the fungicide action of Bialaphos.

Transmission of the PPT resistance through seeds

Transformed tobacco plants expressing the chimeric "sfr" gene present in pGSFR1161 and pGSFR1281 are brought to flowering in the greenhouse. They show a normal fertility.

About 500 F1 seeds of each plant are sown in soil, F1 designating seeds of the first generation, i.e directly issued from the originally transformed plants. When seedlings are 2–3 cm high, they are sprayed with 8 l BASTA$^R$/ha. 7 days later, healthy and damaged plants can be distinguished in a ratio of approximately 3 to 1. this shows that PPT resistance is inherited as a dominant marker encoded by a single locus.

10 resistant F1 seedlings are grown to maturity and seeds are harvested. F2 seedlings are grown as described above and tested for PPT-resistance by spraying BASTA$^R$ at a dose of 8 l/ha. Some of the F1 plants produce F2 seedlings which are all PPT-resistant showing that these plants are homozygous for the resistance gene. The invention also concerns plant cells and plants non-essentially-biologically-transformed with a GS inhibitor-inactivating-gene according to the invention.

In a preferred embodiment of the invention, plant cells and plants are non-biologically-transformed with the "sfr" gene hereabove described.

Such plant cells and plants possess, stably integrated in their genome, a non-variety-specific character which render them able to produce detectable amounts of phosphinotricin-acetyl transferase.

This character confers to the transformed plant cells and plants a non-variety-specific enzymatic activity capable of inactivating or neutralizing GS inhibitors like Bialaphos and PPT.

Accordingly, plant cells and plants transformed according to the invention are rendered resistant against the herbicidal effects of Bialaphos and related compounds.

Since Bialaphos was first described as a fungicide, transformed plants can also be protected against fungal diseases by spraying with the compound several times.

In a preferred embodiment, Bialaphos or related compounds is applied several times, particularly at time intervals of about 20 to 100 days.

The invention also concerns a new process for selectively protecting a plant species against fungal diseases and selectively destroying weeds in a field comprising the steps of treating a field with an herbicide, wherein the plant species contain in their genome a DNA fragment encoding a protein having an enzymatic activity capable of neutralizing or inactivating GS inhibitors and wherein the used herbicide comprises as active ingredient a GS inhibitor.

It comes without saying that the process according to the invention can be employed with the same efficiency, either to only destroy weeds in a field, if plants are not infected with fungi, either to only stop the development of fungi if the latter appears after destruction of weeds.

In a preferred embodiment of the process according to the invention, plant species are transformed with a DNA fragment comprising the "sfr" gene as described hereabove, and the used herbicide is PPT or a related compound.

Accordingly, a solution of PPT or related compound is applied over the field, for example by spraying, several times after emergence of the plant species to be cultivated, until early and late germinating weeds are destroyed.

It is quite evident that before emergence of plant species to be cultivated, the field can be treated with an herbicidal composition to destroy weeds.

On the same hand, fields can be treated even before the plant species to be cultivated are sowed.

Before emergence of the desired plant species, fields can be treated with any available herbicide, including Bialaphos-type herbicides.

After emergence of the desired plant species, Bialaphos or related compound is applied several times.

In a preferred embodiment, the herbicide is applied at time intervals of about from 20 to 100 days.

Since plants to be cultivated are transformed in such a way as to resist to the herbicidal effects of Bialaphos-type herbicides, fields can be treated even after emergence of the cultivated plants.

This is particularly useful to totally destroy early and late germinating weeds, without any effect on the plants to be produced.

Preferably, Bialaphos or related compoud is applied at a dose ranging from about 0.4 to about 1.6 kg/ha, and diluted in a liquid carrier at a concentration such as to enable its application to the field at a rate ranging from about 2 to about 8 l/ha.

There follows examples, given by way of illustration, of some embodiments of the process with different plant species.

Sugarbeets

The North European sugarbeet is planted from March 15 up to April 15, depending upon the weather condition and more precisely on the precipitation and average temperature. the weeds problems are more or less the same in each country and can cause difficulties until the crop closes its canopy around mid-July.

Weed problems can be separated in three situations:

early germination of the grassy weeds, early germinating broadleaved weeds, late germinating broadleaved weeds.

Up to now, pre-emergence herbicides have been successfully used. Such compounds are for example those commercially available under the registered trademarks: PYRAMIN$^R$, GOLTIX$^R$ and VENZAR$^R$. However, the susceptibility to dry weather conditions of these products as well as the lack of residual activity to control late germinating weeds have led the farmer to use post-emergence products in addition to pre-emergence ones.

Table (I) thereafter indicates the active ingredients contained in the herbicidal compositions cited in the following examples.

TABLE (I)

| Commercial Name | Active Ingredient | Formulation |
|---|---|---|
| AVADEX ® | Diallate | EC 400 g/l |
| AVADEX BW ® | Triallate | EC 400 g/l |
| GOLTIX ® | Metamitron | WP 70% |
| RONEET ® | Cycloate | EC 718 g/l |
| TRAMAT ® | Ethofumerate | EC 200 g/l |
| FERVINAL ® | Alloxydime-sodium | SP 75% |
| BASTA ® | Phosphinotricin | 200 g/l |
| PYRAMIN FL ® | Chloridazon | SC 430 g/l |

According to the invention, post-emergence herbicides consist of Bialaphos or related compounds, which offer a good level of growth control of annual grasses (Bromus, Avena spp., Alopecurus, POA) and broadleaves (Galium, Polygonum, Senecio, Solanum, Mercurialis).

Post-emergence herbicides can be applied at different moments of the growth of sugarbeet; at a cotyledon level, two-leave level or at a four-leave level.

Table (II) thereafter represents possible systems of field-treatment, given by way of example.

In those examples, the post-emergence herbicide of the class of Bialaphos used is BASTA$^R$, in combination with different pre-emergence herbicides. Concentrations are indicated in l/ha or kg/ha.

The strains pGSJ260 and pBG39 used hereabove have been deposited on Dec. 12nd, 1985, at the "German Collection of Micro-organisms" (DEUTSCHE SAMMLUNG YON MIKROORGANISMEN) at Göttingen, Germany. They received the deposition numbers DSM 3 606 and DSM 3 607 respectively.

TABLE (II)

POSSIBLE WEEDCONTROL SYSTEMS IN SUGARBEETS, BASED ON THE USE OF BASTA ®, PROVIDING BEETS ARE MADE RESISTANT AGAINST THE LATTER CHEMCIAL (in lt or kg/ha).

| Pre-sowing | Pre-emergence | Cotyledons | Two-leaves | | Four leaves | |
|---|---|---|---|---|---|---|
| 1. AVADEX ® 3.5 lt | — | BASTA ® 3 lt | BASTA ®/tramat 3 lt | 1.5 lt | — | |
| 2. AVADEX ® 3.5 lt | GOLTIX ® 4 kg | — | — | | — | |
| 3 RONEET ® 4 lt | GOLTIX ® 5 kg | — | — | | — | |
| 4. RONEET ® 4 lt | GOLTIX ® 2.5 kg | — | BASTA ® 3 lt | | — | |
| 5. TRAMAT ® 5 lt | — | — | BASTA ® 3 lt | | BASTA ®/GOLTIX ® 2 lt | 2 kg |
| 6. — | GOLTIX ® 2.5 kg | — | BAST ® 3 lt | | — | |
| 7. — | — | BASTA ®/tramat 3 lt  1.7 lt | — | | BASTA ®/GOLTIX ® 3 lt | 2 kg |
| 8. PYRAMIN ® 6 lt | — | BASTA ® 3 lt | Venzar 1 kg | | — | |
| 9. — | — | BASTA ® 3 lt | BASTA ®/GOLTIX ® 3 lt | 2 kg | — | |
| 10. DIALLATE ® 3.5 lt | PYRAMIN ® 6 lt | — | BASTA ®/Metamitron 3 lt | 1 kg | — | |

Potatoes

Potatoes are grown in Europe on about 8.10$^6$ Ha. The major products used for weed control are Linuron/monolinuron or the compound commercially available under the denomination METRABUZIN These products perform well against most weed species.

However, weeds such as Galium and Solanum plus late germinating Chenopodium and Polygonum are not always effectively controlled, while control of the annual grasses is also sometime erratic.

Once again, late germinating broadleaved weeds are only controllable by post-emergence applications of herbicides such as BASTA$^R$.

Table (III) thereafter represents some examples given by way of example of field-treatment in the case of potatoes.

TABLE (III)

Weeds control systems in potatoes, based on the use of BASTA ®, providing potatoes are rendered resistant to BASTA ®.
Linuron + monolinuron (375 g + 375 g/ha) prior to emergence

| | |
|---|---|
| BASTA ® | 3–4 lt/ha after emergence (5–15 cm) |
| BASTA ®/fluazifop-butyl | 3–4 lt/ha + 2 lt/ha after emergence (5–15 cm) |
| Linuron | WP 50% (AFALON ®) |
| Monolinuron | WP 47.5% (ARESSIN ®) |
| fluazifop-butyl | EL 250 g/l (FUSILADE ®) |

Figure 8:
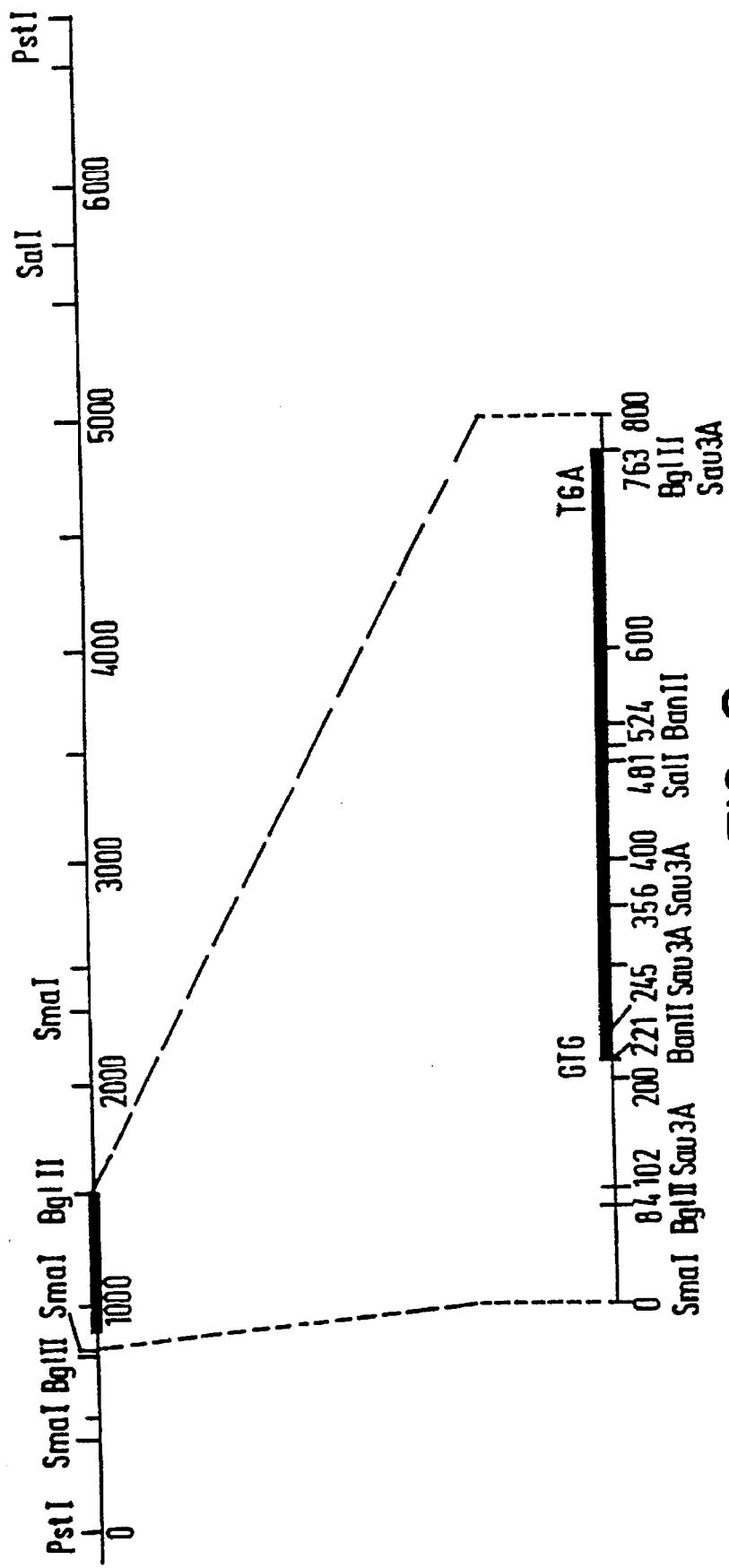

Further embodiments of the invention are described hereafter with reference to the figures in which:

FIG. 8 shows the restriction map of a plasmid pJS1 containing another Bialaphos-resistance-gene;

FIG. 9 shows the nucleotide sequence of the "sfrsv" gene containing the resistance gene;

FIG. 10 shows the amino acid homology of "sfrsv" gene and "sfr" gene,

FIG. 11 shows the construction of a plasmid, given by way of example, which contains the "sfrsv" gene and suitable for the transformation of plant cells.

Another Bialaphos-resistance-gene has been isolated form another Bialaphos-producing-strains, i.e. *streptomyces viridochromogenes*. This second resistance-gene is thereafter designated by "sfrsv" gene.

This second preferred DNA fragment according to the invention, for the subsequent transformation of plant cells, consists of a nucleotide sequence coding for at least part of a polypeptide having the following sequence:

| V | $ | P | E | R | R | P | V | E | I | R | P | A | T | A | A | D | M |
|---|---|---|---|---|---|---|---|---|---|---|---|---|---|---|---|---|---|
| A | A | V | C | D | I | V | N | H | Y | I | E | T | S | T | V | N | F |
| R | T | E | P | Q | T | P | Q | E | W | I | D | D | L | E | R | L | Q |
| D | R | Y | P | W | L | V | A | E | V | E | G | V | V | A | G | I | A |
| Y | A | G | P | W | K | A | R | N | A | Y | D | W | T | V | E | S | T |
| V | Y | V | S | H | R | H | Q | R | L | G | L | G | S | T | L | Y | T |
| H | L | L | K | S | M | E | A | Q | G | F | K | $ | V | V | A | V | I |
| G | L | P | N | D | P | S | V | R | L | H | E | A | L | G | Y | T | A |
| R | G | T | L | R | A | A | G | Y | K | H | G | G | W | H | D | V | G |
| F | W | Q | R | D | F | E | L | P | A | P | P | R | P | V | R | P | V |
| T | Q | I | * | | | | | | | | | | | | | | | which part of said polypeptide is of sufficient length to confer protection against Bialaphos-"plant-protecting-capability"-, to plant cells, when incorporated genetically and expressed therein. Reference will also be made hereafter to the "plant-protecting-capability" against Bialaphos of the abovesaid nucleotide sequence.

Meaning of the designation of amino acids by a single letter is given therafter.

| Alanine | A | Leucine | L |
|---|---|---|---|
| Arginine | R | Lysine | K |
| Asparagine | N | Methionine | M |
| Aspartic Acid | D | Phenylalanine | F |
| Cysteine | C | Proline | P |
| Cystine | C | Serine | S |
| Glycine | G | Threonine | T |
| Glutamic Acid | E | Tryptophan | W |
| Glutamine | Q | Tyrosine | Y |
| Histidine | H | Valine | V |
| Isoleucine | I | | |

This second preferred DNA fragment consists of the following nucleotide sequence:

TAAAGAGGTGCCCGCCACCCGCTTTCGCAGAACACCGAAGGAGACCACAC

↓

GTGAGCCCAGAACGACGCCCGGTCGAGATCCGTCCCGCCACCGCCGCCGA

CATGGCGGCGGTCTGCGACATCGTCAATCACTACATCGAGACGAGCACGG

TCAACTTCCGTACGGAGCCGCAGACTCCGCAGGAGTGGATCGACGACCTG

GAGCGCCTCCAGGACCGCTACCCCTGGCTCGTCGCCGAGGTGGAGGGCGT

CGTCGCCGGCATCGCCTACGCCGGCCCCTGGAAGGCCCGCAACGCCTACG

ACTGGACCGTCGAGTCGACGGTGTACGTCTCCCACCGGCACCAGCGGCTC

GGACTGGGCTCCACCCTCTACACCCACCTGCTGAAGTCCATGGAGGCCCA

GGGCTTCAAGAGCGTGGTCGCCGTCATCGGACTGCCCAACGACCCGAGCG

TGCGCCTGCACGAGGCGCTCGGATACACCGCGCGCGGGACGCTGCGGGCA

GCCGGCTACAAGCACGGGGGCTGGCACGACGTGGGGTTCTGGCAGCGCGA

CTTCGAGCTGCCGGCCCCGCCCCGCCCCGTCCGGCCCGTCACACAGATCT
↑

GAGCGGAGAGCGCATGGC.

or of a part thereof expressing a polypeptide having plant-protecting capability against Bialaphos;

There follows hereafter the description of experiments carried out for the isolation of the "sfrsv" resistance gene, the construction of expression vectors which contain the resistance gene and which allow the subsequent transformation of plant cells, in order to render them resistant to GS inhibitors.

Cloning of the Bialaphos-resistance-"sfrsv" Gene from *Streptomyces viridochromogenes*

The strain *streptomyces viridochromogenes* DSM 40736 (ref 1) was grown and total DNA of this strain was prepared according to standard techniques. DNA samples were digested respectively with FstI, SmaI and Sau3AI in three different reactions and separated on an agarose gel, together with plasmid DNA from pGSR1 (FIG. 5B) digested with BamHI. In a Southern analysis the DNA was blotted on a nitrocellulose filter and hybridized with the labbeled BamHI fragment from pGSR1 containing the "sfr" gene. In all four lanes of the gel, a restriction fragment was showing strong homology with the probe: a PstI fragment of about 3 kb, a SmaI fragment of about 1.2 kb and Sau3AI fragment of 0.5 kb. In order to clone this gone, PstI restriction fragments were directly cloned in the *Escherichia coli* vector pUC8. 3000 colonies obtained after transformation were transferred to nitrocellulose filters, and hybridized with the "sfr" probe. Positive candidates were further tested for their growth on minimal medium plates containing 300 µg/ml PPT. One transformant that grew on PPT-containing-medium was further analysed. The plasmid map and relevant restriction sites of this plasmid pJS1 are represented in FIG. 8. The strain MC1061 (pJS1) has been deposited on Mar. 06, 1987 at the DEUTSCHE SAMMLUNG VON MIKROORGANISMEN (DSM) under deposition number DSM 4023. The clone restriction fragment has been sequenced according to the Maxam and Gilbert method and the coding region of the gene could be identified through homology. The sequence of the "sfrsv" gene is represented in FIG. 9 and the homology on the nucleotide and amino acid sequence level with "sfr" gene is shown in FIG. 10.

Expression of the "sfrsv" Gene

A "sfrsv gene cassette" was also constructed to allow subsequent cloning in plant expression vectors. A BanII-BulII fragment containing the "sfrsv" coding region without the initiation codon GTG was isolated from pJS1. This fragment was ligated in the vector pLK56-2 digested with NcoI and BglII, together with a synthetic oligonucleotide 5'-CATGAGCC-3', similar with the one described for "sfr" gene and shown in FIG. 5. The construction of pGSR1SV is schematically shown in FIG. 11. Since similar cassettes of both genes are present in respectively pGSR1 and pGSR1SV, previous described constructions for the expression of the "sfr" gene in plants can be repeated.

Enzymatic analysis of crude extracts from *E. coli* strains carrying plasmid pGSR1SV demonstrated the synthesis of an acetylase which could acetylate PPT. This was shown by thin layer chromotography of the reaction porducts.

The "sfrsv" gene was then inserted into the plasmid vector pGSJ260 (FIG. 4B) under the control of the CaMV 35s promoter, to yield a plasmid pGS2SV, similar to pGSR2 (FIG. 6A) except that the "sfrsv" gene is substituted for the "sfr" gene.

It is clear that herbicide resistance genes of the above type may be obtained from many other microorganisms that produce PPT or PPT derivatives. Herbicide resistance gene can then be incorporated in plant cells with a view of protecting them against the action of such Glutamine Synthetase inhibitors. For instance, a Bialaphos-resistance-gene is obtained from Kitasotosporia (ref. 15).

Transformed plant cells and plants which contain the "sfrsv" resistance gene can be obtained with plasmid pGSR2SV, using the same Agrobacterium-mediated-transformation system as hereabove described for the transformation of different plant species with the "sfr" gene.

Plants are regenerated and tested for their resistance with similar spraying tests as described hereabove. All plants behaved similarly and show resistance against herbicides consisting of glutamine synthetase inhibitors.

Finally, the inventors also pertains to the combination of the plants resistant to an inhibitor of glutamine synthetase as defined above with the corresponding inhibitor of glutamine synthetase for use in the production of cultures of said plants free form weeds.

REFERENCES

1. BAYER et al., HELVETICA CHEMICA ACTA, 1972
2. WAKABAYASHI K. and MATSUNAKA S., Proc. 1982, British Crop Protection Conference, 439–450
3. M. MASON et al., PHYTOCHEMISTRY, 1982, vol. 21, n°4, p. 855–857.
4. C. J. THOMPSON et al., NATURE, Jul. 31, 1980, vol. 286, n°5 772, p. 525–527
5. C. J. THOMPSON et al., JOURNAL OF BACTERIOLOGY, August 1982, p. 678–685
6. C. J. THOMPSON et al., GENE 20, 1982, p. 51–62
7. C. J. THOMPSON et al., MOL. GEN. GENET., 1984, 195, p. 39–43
8. TOWBIN et al., PROC. NATL. ACAD. SCI. USA, 1979, 76, p. 4 350–4 354
9. METHODS OF ENZYMOLOGY, V.XLIII, p. 737–755
10. DEBLAERE H. et al., 1985, Nucl. Acid. Res., 13, 1 477
11. BOTTERMAN J., February 1986, Ph. D. Thesis, State University of Ghent
12. DEBLAERE R., february 1986, Ph. D Thesis, Free University of Brussel, Belgium
13. VELTEN et al, EMBO J. 1984, vol. 3, n°12, p. 2 723–2 730
14. CHATER et al, Gene cloning in Streptomyces. Curr. Top. Microbiol. Immunol., 1982, 96, p. 69–75
15. OMURA et al, J. of Antibiotics, Vol. 37, 8, 939–940, 1984
16. MURAKAMI et al, Mol. Gen. Genet., 205, 42–50, 1986
17. MANDERSCHEID and WILD, J. Plant Phys., 123, 135–142, 1986

We claim:

1. A vector comprising a chimeric gene comprising in sequence:
   (a) a promoter recognized by polymerases of a plant cell; and
   (b) a DNA fragment encoding a protein with acetyltransferase activity on a glutamine synthetase inhibitor, wherein said protein is capable of inactivating said glutamine synthetase inhibitor in a plant cell.

2. The vector of claim 1, wherein said DNA fragment encodes a protein with phosphinothricin acetyltransferase activity.

3. The vector of claim 2, wherein said DNA fragment is obtained from a Streptomyces species.

4. The vector of claim 3, wherein said DNA is obtained from *Streptomyces hygroscopicus* or *Streptomyces viridochromogenes*.

5. The vector of claim 2, wherein said DNA fragment encoding a protein with phosphinothricin acetyltransferase activity has a molecular weight of about 22 kD.

6. The vector of claim 2, wherein said DNA fragment encodes a protein comprising the amino acid sequence:

| X | Ser | Pro | Glu | Arg | Arg | Pro | Ala | Asp | Ile | Arg | Arg | Ala | Thr | Glu | Ala |
|---|-----|-----|-----|-----|-----|-----|-----|-----|-----|-----|-----|-----|-----|-----|-----|
| Asp | MET | Pro | Ala | Val | Cys | Thr | Ile | Val | Asn | His | Tyr | Ile | Glu | Thr | Ser |
| Thr | Val | Asn | Phe | Arg | Thr | Glu | Pro | Gln | Glu | Pro | Gln | Glu | Trp | Thr | Asp |
| Asp | Leu | Val | Arg | Leu | Arg | Glu | Arg | Tyr | Pro | Trp | Leu | Val | Ala | Glu | Val |
| Asp | Gly | Glu | Val | Ala | Gly | Ile | Ala | Tyr | Ala | Gly | Pro | Trp | Lys | Ala | Arg |
| Asn | Ala | Tyr | Asp | Trp | Thr | Ala | Glu | Ser | Thr | Val | Tyr | Val | Ser | Pro | Arg |
| His | Gln | Arg | Thr | Gly | Leu | Gly | Ser | Thr | Leu | Tyr | Thr | His | Leu | Leu | Lys |
| Ser | Leu | Glu | Ala | Gln | Gly | Phe | Lys | Ser | Val | Val | Ala | Val | Ile | Gly | Leu |
| Pro | Asn | Asp | Pro | Ser | Val | Arg | Met | His | Glu | Ala | Leu | Gly | Tyr | Ala | Pro |
| Arg | Gly | Met | Leu | Arg | Ala | Ala | Gly | Phe | Lys | His | Gly | Asn | Trp | His | Asp |
| Val | Gly | Phe | Trp | Gln | Leu | Asp | Phe | Ser | Leu | Pro | Val | Pro | Pro | Arg | Pro |
| Val | Leu | Pro | Val | Thr | Glu | Ile | | | | | | | | | | in which X is Met or Val, or a part of said protein having phosphinothricin acetyltransferase activity.

7. The vector of claim 6, wherein said DNA fragment comprises the nucleotide sequence:

```
NTG AGC CCA GAA CGA CGC CCG GCC GAC ATC CGC CGT GCC ACC GAG GCG
GAC ATG CCG GCG GTC TGC ACC ATC GTC AAC CAC
TAC ATC GAG ACA AGC ACG GTC AAC TTC CGT ACC GAG CCG CAG GAA CCG
CAG GAG TGG ACG GAC GAC CTC GTC CGT CTG CGG GAG CGC TAT CCC TGG
CTC GTC GCC GAG GTG GAC GGC GAG GTC GCC GCC ATC GCC TAC GCG GGC
CCC TGG AAG GCA CGC AAC GCC TAC GAC TGG ACG GCC GAG TCG ACC GTG
TAC GTC TCC CCC CGC CAC CAG CGG ACG GGA CTG GGC TCC ACG CTC TAC
ACC CAC CTG CTG AAG TCC CTG GAG GCA CAG GGC TTC AAG AGC GTG GTC
GCT GTC ATC GGG CTG CCC AAC GAC CCG AGC GTG CGC ATG CAC GAG GCG
CTC GGA TAT GCC CCC CGC GGC ATG CTG CGG GCG GCC GGC TTC AAG CAC
GGG AAC TGG CAT GAC GTG GGT TTC TGG CAG CTG GAC TTC AGC CTG CCG
GTA CCG CCC CGT CCG GTC CTG CCC GTC ACC GAG ATC
``` in which N is A or G.

8. The vector of claim 1, wherein said promoter is a 35S promoter of Cauliflower Mosaic Virus, a TR1' promoter, a TR2' promoter or a promoter of a gene encoding a Rubisco small subunit.

9. The vector of claim 2, wherein said promoter is a 35S promoter of Cauliflower Mosaic Virus, a TR1' promoter, a TR2' promoter or a promoter of a gene encoding a Rubisco small subunit.

10. The vector of claim 6, wherein said promoter is a 35S promoter of Cauliflower Mosaic Virus, a TR1' promoter, a TR2' promoter or a promoter of a gene encoding a Rubisco small subunit.

11. The vector of claims 2 or 6, which further comprises a first DNA encoding a chloroplast transit peptide between said promoter and said DNA fragment.

12. The vector of claim 11, in which said first DNA is from a gene encoding the Rubisco small subunit.

13. The vector of claims 2 or 6 which further comprises a 3' untranslated end including a polyadenylation signal.

14. The vector of claim 13, wherein said 3' untranslated end is from a T-DNA gene of *Agrobacterium tumefaciens*.

15. The vector of claims 2 or 6 wherein said DNA fragment and said promoter are located between T-DNA border sequences to enable transfer of said DNA fragment and said promoter to a plant cell.

16. The vector of claim 15, which is a modified Ti-plasmid.

17. The vector of claims 2 or 6 which is capable of replicating in a bacterium.

18. The vector of claim 17, which is capable of replicating in *E. coli*.

19. The vector of claim 17, which is capable of replicating in *Agrobacterium tumefaciens*.

20. A vector comprising a DNA fragment encoding a protein comprising the amino acid sequence:

| X | Ser | Pro | Glu | Arg | Arg | Pro | Ala | Asp | Ile | Arg | Arg | Ala | Thr | Glu | Ala |
|---|-----|-----|-----|-----|-----|-----|-----|-----|-----|-----|-----|-----|-----|-----|-----|
| Asp | MET | Pro | Ala | Val | Cys | Thr | Ile | Val | Asn | His | Tyr | Ile | Glu | Thr | Ser |
| Thr | Val | Asn | Phe | Arg | Thr | Glu | Pro | Gln | Glu | Pro | Gln | Glu | Trp | Thr | Asp |
| Asp | Leu | Val | Arg | Leu | Arg | Glu | Arg | Tyr | Pro | Trp | Leu | Val | Ala | Glu | Val |
| Asp | Gly | Glu | Val | Ala | Gly | Ile | Ala | Tyr | Ala | Gly | Pro | Trp | Lys | Ala | Arg |
| Asn | Ala | Tyr | Asp | Trp | Thr | Ala | Glu | Ser | Thr | Val | Tyr | Val | Ser | Pro | Arg |
| His | Gln | Arg | Thr | Gly | Leu | Gly | Ser | Thr | Leu | Tyr | Thr | His | Leu | Leu | Lys |
| Ser | Leu | Glu | Ala | Gln | Gly | Phe | Lys | Ser | Val | Val | Ala | Val | Ile | Gly | Leu |
| Pro | Asn | Asp | Pro | Ser | Val | Arg | Met | His | Glu | Ala | Leu | Gly | Tyr | Ala | Pro |
| Arg | Gly | Met | Leu | Arg | Ala | Ala | Gly | Phe | Lys | His | Gly | Asn | Trp | His | Asp |
| Val | Gly | Phe | Trp | Gln | Leu | Asp | Phe | Ser | Leu | Pro | Val | Pro | Pro | Arg | Pro |
| Val | Leu | Pro | Val | Thr | Glu | Ile | | | | | | | | | | in which X is Met or Val, or a part of said protein having phosphinothricin acetyltransferase activity.

21. The vector of claim 20, wherein said DNA fragment comprises the nucleotide sequence:

```
NTG AGC CCA GAA CGA CGC CCG GCC GAC ATC CGC CGT GCC ACC GAG GCG
GAC ATG CCG GCG GTC TGC ACC ATC GTC AAC CAC TAC ATC GAG ACA AGC
ACG GTC AAC TTC CGT ACC GAG CCG CAG GAA CCG CAG GAG TGG ACG GAC
GAC CTC GTC CGT CTG CGG GAG CGC TAT CCC TGG CTC GTC GCC GAG GTG
GAC GGC GAG GTC GCC GGC ATC GCC TAC GCG GGC CCC TGG AAG GCA CGC
AAC GCC TAC GAC TGG ACG GCC GAG TCG ACC GTG TAC GTC TCC CCC CGC
CAC CAG CGG ACG GGA CTG GGC TCC ACG CTC TAC ACC CAC CTG CTG AAG
TCC CTG GAG GCA CAG GGC TTC AAG AGC GTG GTC GCT GTC ATC GGG CTG
CCC AAC GAC CCG AGC GTG CGC ATG CAC GAG GCG CTC GGA TAT GCC CCC
CGC GGC ATG CTG CGG GCG GCC GGC TTC AAG CAC GGG AAC TGG CAT GAG
GTG GGT TTC TGG CAG CTG GAC TTC AGC CTG CCG GTA CCG CCC CGT CCG
GTC CTG CCC GTC ACC GAG ATC
``` in which N is A or G.

22. The vector of claims 20 or 21 which further comprises a promoter recognized by polymerases of a host cell, wherein said promoter controls expression of a coding region comprising said DNA fragment.

23. The vector of claim 22, wherein said promoter is heterologous to said DNA fragment.

24. The vector of claim 22, wherein said promoter is recognized by the polymerase of *E. coli*.

25. A vector comprising a DNA fragment encoding a protein with acetyltransferase activity on a glutamine synthetase inhibitor, wherein said protein is capable of inactivating said glutamine synthetase inhibitor in a plant cell.

26. The vector of claim 25, wherein said DNA fragment encodes a protein with phosphinothricin acetyltransferase activity.

27. The vector of claim 26, wherein said DNA fragment is obtained from a Streptomyces species.

28. The vector of claim 27, wherein said DNA is obtained from *Streptomyces hygroscopicus* or *Streptomyces viridochromogenes*.

29. The vector of claim 26, wherein said DNA fragment encodes a protein with phosphinothricin acetyltransferase activity having a molecular weight of about 22 kD.

30. The vector of any one of claims 25, 26, 27, 28 or 29, wherein said DNA fragment is under control of a promoter recognized by polymerases of a host cell, wherein said promoter is heterologous to said DNA fragment.

* * * * *

UNITED STATES PATENT AND TRADEMARK OFFICE
CERTIFICATE OF CORRECTION

PATENT NO.    : 5,648,477
DATED         : July 15, 1997
INVENTOR(S)   : Jan LEEMANS et al It is certified that error appears in the above-indentified patent and that said Letters Patent is hereby corrected as shown below:

On the cover page under Assignee after Plant Genetic Systems, N.V., Gent, Belgium please add -- and Biogen, Inc., Cambridge, Massachusetts, U.S.A.--.

On the cover page under related U.S. Application Data after abandoned, please add --filed as PCT EP 87/001 141, Mar. 11, 1987--

On cover page 2, under Other Publications, last publication listed (Murakami et al.), after Mol. Gen. Genet. 205:42-50 please insert --(1986)--.

Column 2 of the Letters Patent in line 9 please delete the word "media" and insert the word --medium--.

UNITED STATES PATENT AND TRADEMARK OFFICE
CERTIFICATE OF CORRECTION

PATENT NO. : 5,648,477
DATED : July 15, 1997
INVENTOR(S) : Jan LEEMANS et al

It is certified that error appears in the above-identified patent and that said Letters Patent is hereby corrected as shown below:

Column 2 in line 37 please delete the number "24.705" and insert the number --21.705--.

Column 6 in line 55 please delete the word "inactivationg" and insert the word --inactivation--.

Column 7 in line 35 please delete the word "vital" and insert the word --viral--.

Column 8 in line 24 after the name Schreier please delete the word "and" and insert the word --et--.

Column 10 in line 27 please delete "pBO39" and insert --pBG39--.

Column 11 in line 57 please delete "pUC9" and insert --pUC19--.

Column 16 in line 39 please delete "(pUV2260)" and insert --(pGV2260)--.

Column 17 in line 62 please delete "plasmides" and insert --plasmids--.

Column 25 in TABLE (II) number 6. please delete "BAST®" and insert --BASTA®--.

Column 26 in line 2 please delete "12nd." and insert --12th--.

UNITED STATES PATENT AND TRADEMARK OFFICE
CERTIFICATE OF CORRECTION

PATENT NO. : 5,648,477
DATED : July 15, 1997
INVENTOR(S) : Jan LEEMANS et al

It is certified that error appears in the above-identified patent and that said Letters Patent is hereby corrected as shown below:

Column 26 in line 4 please delete "YON" and insert --VON--.

Column 27 in the first table in line 1 across please delete "$" and insert --S--.

Column 27 in the first table in line 7 across please delete "$" and insert --S--.

Column 28 in line 67 please delete "labbeled" and insert --labeled--.

Column 29 in line 5 please delete "gone" and insert --gene--.

Column 29 in line 26 please delete "BuII" and insert --BglII--.

Column 30 in line 3 please delete "form" and insert --from--.

Column 31 in the first sequence listing in line 8 delete "lle" and insert --Ile--.

Column 31 in the first sequence listing in line 12 delete "lle" and insert --Ile--.

Column 32 in the first sequence listing in line 5 delete "lle" and insert --Ile--.

Column 32 in the first sequence listing in line 12 delete "lle" and insert --Ile--.

UNITED STATES PATENT AND TRADEMARK OFFICE
CERTIFICATE OF CORRECTION

PATENT NO. : 5,648,477
DATED : July 15, 1997
INVENTOR(S) : Jan LEEMANS et al

It is certified that error appears in the above-identified patent and that said Letters Patent is hereby corrected as shown below:

Column 33 in the first sequence listing in line 10 delete the "GAG" and insert --GAC--.

Signed and Sealed this

Nineteenth Day of January, 1999

Attest:

Attesting Officer

*Acting Commissioner of Patents and Trademarks*